(12) United States Patent
Drobnik et al.

(10) Patent No.: US 7,041,048 B2
(45) Date of Patent: May 9, 2006

(54) APPARATUS AND METHOD FOR DOSE ADMINISTRATION IN BRACHYTHERAPY

(75) Inventors: Christopher D. Drobnik, Wauconda, IL (US); Michael W. Drobnik, Downers Grove, IL (US); Scott C. Jones, Bloomingdale, IL (US); Dave Sieracki, Elmhurst, IL (US)

(73) Assignee: SourceTech Medical, LLC, Carol Stream, IL (US)

( * ) Notice: Subject to any disclaimer, the term of this patent is extended or adjusted under 35 U.S.C. 154(b) by 27 days.

(21) Appl. No.: 10/272,803

(22) Filed: Oct. 16, 2002

(65) Prior Publication Data

US 2004/0077919 A1 Apr. 22, 2004

(51) Int. Cl.
*A61N 5/00* (2006.01)
(52) U.S. Cl. .......................................... 600/7
(58) Field of Classification Search ............... 600/7, 600/8, 439, 1, 2–6, 427, 431, 407, 434, 459; 604/60, 173, 57, 64, 891.1, 63, 59, 61, 62; 221/4; 128/920, 922; 250/506.1, 507.1; 348/7
See application file for complete search history.

(56) References Cited

U.S. PATENT DOCUMENTS

| | | | | |
|---|---|---|---|---|
| 4,086,914 A | * | 5/1978 | Moore | 600/7 |
| 4,167,179 A | * | 9/1979 | Kirsch | 600/7 |
| 4,402,308 A | * | 9/1983 | Scott | 600/7 |
| 4,451,254 A | | 5/1984 | Dinius et al. | |
| 4,700,692 A | * | 10/1987 | Baumgartner | 600/7 |
| 4,759,345 A | | 7/1988 | Mistry | |
| 4,897,076 A | | 1/1990 | Puthawala et al. | |
| 5,120,973 A | | 6/1992 | Rohe et al. | |
| 5,242,373 A | | 9/1993 | Scott et al. | |
| 5,391,139 A | * | 2/1995 | Edmundson | 600/7 |
| 5,460,592 A | | 10/1995 | Langton et al. | |
| 5,860,909 A | | 1/1999 | Mick et al. | |
| 5,906,574 A | | 5/1999 | Kan | |
| 5,928,130 A | | 7/1999 | Schmidt | |
| 5,938,583 A | * | 8/1999 | Grimm | 600/7 |
| 6,007,474 A | | 12/1999 | Rydell | |
| 6,102,844 A | | 8/2000 | Ravins et al. | |
| 6,113,529 A | | 9/2000 | Shi | |
| 6,213,932 B1 | | 4/2001 | Schmidt | |
| 6,221,003 B1 | | 4/2001 | Sierocuk et al. | |
| 6,251,059 B1 | * | 6/2001 | Apple et al. | 600/3 |
| 6,258,056 B1 | | 7/2001 | Turley et al. | |
| 6,267,718 B1 | | 7/2001 | Vitali et al. | |
| 6,270,472 B1 | | 8/2001 | Antaki et al. | |
| 6,358,195 B1 | | 3/2002 | Green et al. | |
| 6,361,487 B1 | | 3/2002 | Green et al. | |
| 6,428,463 B1 | | 8/2002 | Ravins et al. | |
| 6,432,035 B1 | | 8/2002 | Ravins et al. | |
| 6,450,937 B1 | | 9/2002 | Mercereau et al. | |
| 6,454,696 B1 | * | 9/2002 | Kindlein et al. | 600/7 |
| 6,472,675 B1 | * | 10/2002 | White et al. | 250/506.1 |
| 6,508,755 B1 | | 1/2003 | Ravins et al. | |

(Continued)

FOREIGN PATENT DOCUMENTS

EP 1 070 519 * 1/2001

(Continued)

*Primary Examiner*—John P. Lacyk
(74) *Attorney, Agent, or Firm*—Patti & Brill, LLC

(57) ABSTRACT

An apparatus and method for administering a dose in brachytherapy procedures having a handheld housing containing a dose of radioactive seeds adapted for use in a brachytherapy treatment and a display for observing information about the dose and viewing the dose or components of the dose.

99 Claims, 15 Drawing Sheets

U.S. PATENT DOCUMENTS

| | | | |
|---|---|---|---|
| 6,512,942 B1 * | 1/2003 | Burdette et al. | 600/427 |
| 6,537,192 B1 | 3/2003 | Elliott et al. | |
| 6,561,967 B1 | 5/2003 | Schmidt | |
| 6,572,525 B1 | 6/2003 | Yoshizumi | |
| 6,572,527 B1 * | 6/2003 | Steele et al. | 600/7 |
| 6,575,890 B1 * | 6/2003 | Kaplan et al. | 600/7 |
| 6,582,354 B1 * | 6/2003 | Ellard | 600/8 |
| 6,592,508 B1 | 7/2003 | Ravins et al. | |
| 2002/0007140 A1 | 1/2002 | Kaplan et al. | |
| 2002/0032360 A1 | 3/2002 | Fontayne et al. | |
| 2002/0193656 A1 | 12/2002 | Ravins et al. | |
| 2003/0084988 A1 | 5/2003 | Terwilliger et al. | |
| 2003/0220533 A1 | 11/2003 | Pedersen et al. | |

FOREIGN PATENT DOCUMENTS

| | | | |
|---|---|---|---|
| WO | WO 01/93945 | * | 12/2001 |
| WO | WO 02/34325 | * | 5/2002 |

* cited by examiner

| NEEDLE NUMBER | RETRACTION (CM) | HOLE LOCATION | NUMBER SEEDS |
|---|---|---|---|
| 1 | 1.00 | D4.0 | 2 |
| 2 | 2.50 | b3.5 | 1 |
| 3 | 0.50 | c3.5 | 4 |
| 4 | 0.50 | d3.5 | 4 |
| 5 | 1.50 | e3.5 | 2 |
| 6 | 1.00 | C3.0 | 4 |
| • 7 | 0.00 | D3.0 | 2 |
| • 8 | 0.00 | E3.0 | 3 |
| 9 | 1.00 | F3.0 | 3 |
| 10 | 1.50 | B2.5 | 2 |
| • 11 | 0.50 | d2.5 | 2 |
| • 12 | 0.50 | e2.5 | 2 |
| 13 | 2.50 | f2.5 | 1 |
| 14 | 1.00 | B2.0 | 3 |
| • 15 | 0.00 | C2.0 | 4 |
| • 16 | 0.00 | D2.0 | 4 |
| • 17 | 0.00 | E2.0 | 4 |
| 18 | 0.00 | F2.0 | 4 |
| 19 | 1.50 | a1.5 | 2 |
| 20 | 0.00 | B1.5 | 1 |
| • 21 | 0.50 | b1.5 | 2 |
| • 22 | 0.50 | c1.5 | 3 |
| 23 | 0.50 | d1.5 | 1 |
| 24 | 0.50 | e1.5 | 4 |
| 25 | 0.50 | f1.5 | 3 |
| 26 | 1.00 | B1.0 | 2 |
| 27 | 1.00 | F1.0 | 2 |

• SPECIAL LOADING

FIG. 1

APPARATUS AND METHOD FOR DOSE ADMINISTRATION IN BRACHYTHERAPY

BACKGROUND

Bodily cancers are commonly treated using radiation therapy, which employs radiation to kill cancer cells. One form of radiation therapy is brachytherapy. The treatment of brachytherapy places the source of radiation in direct contact with the afflicted tissue. A common brachytherapy treatment is the implantation of radioactive seeds in the prostate gland to kill prostate cancer cells. The physician employs tools such as ultrasounds, computerized axial tomography ("CAT") scans, and X-ray images in concert with dose-planning computer software programs to evaluate the medical condition of the patient. The physician constructs an optimal treatment plan to evenly distribute radiation throughout the tissue. Proper seed placement is important for controlling the distribution of radiation evenly throughout the entire prostate gland. Placing the radioactive seeds too close together may result in a portion of the prostate receiving too much radiation. Not placing enough seeds in portions of the tissue may result in a region in which the strength of the radiation is insufficient to kill cancer cells.

The physician may insert seeds of the same or different radioactive strengths in pre-selected locations of the tissue. The seeds are inserted into the tissue through an implantation needle, also known as a brachytherapy needle. Multiple brachytherapy needles are required to insert the seeds into multiple locations of the tissue. Each brachytherapy needle inserts a plurality of seeds. An average brachytherapy treatment involves the implantation of approximately 80 to 100 seeds. One way physicians can achieve the axial seed-to-seed spacing required by the treatment plan is to place non-radioactive spacers between the radioactive seeds.

One technique for implanting the seeds involves manually loading the seeds one by one into brachytherapy needles along with spacers in the order prescribed by the treatment plan. The physician then inserts a loaded brachytherapy needle into a specific area of tissue to be treated. A pushrod is guided into the channel of the brachytherapy needle. The physician withdraws the brachytherapy needle while holding the pushrod in place. The seeds are pushed out of the needle and remain inside the afflicted tissue. Multiple rows of seeds and spacers are used to treat an area of tissue, with each position in a row requiring a different brachytherapy needle loaded with seeds and spacers as specified by the physician's plan. Most treatment plans require twenty or more needles loaded with various combinations of seeds and spacers. The management of twenty or more loaded needles presents organizational and management issues associated with the handling of such a large number of needles and includes the inherent risk of handling radioactive materials.

Needles which are loaded prior to the operation must be plugged to prevent the seeds from spilling out during transport or operating room setup. The needles themselves provide limited radiation shielding, requiring the needles to be packaged in a shielded container once loaded.

To place the seeds in the tissue according to the physician's plan, the needle may be releasably attached to a fixed base member (template). The needle is movable within a plurality of positions with respect to the base member with the plurality of positions corresponding to the locations in which the physician desires placement of the seeds and spacers. Those skilled in the art will understand the use of templates and needle grids in the administration treatments in brachytherapy.

The seeds and spacers are small and difficult to handle. The radioactive seeds are a hazardous material and prolonged contact with the needles containing the radioactive seeds is not desirable. Loading seeds and spacers into the individual brachytherapy needles is a time consuming process that increases the time that the medical staff is exposed. The needle loading process must be repeated for each needle used in the treatment. After the needles are loaded, identifying the arrangement of seeds and spacers in the needle and the strength of the seeds requires that the needles be unloaded, inspected, and reloaded. The loaded needles require a shielded container for transport. The seeds may also fall out of the needle, for example due to plug failure. This causes the medical staff to locate, reload, and resterlize the radioactive seeds. Repeated handling of the radioactive seeds by the medical staff increases exposure time.

A technique exists using cartridges to insert the seeds and spacers into the brachytherapy needle. The seeds and spacers are placed in the desired order in a cartridge, which then detachably couples to the brachytherapy needle. The physician then transfers the seeds and spacers from the cartridge into the brachytherapy needle and removes the cartridge from the needle. The brachytherapy needle can then either be loaded into a shielded transport container or, if loaded in the operating room, inserted directly into the afflicted tissue. The physician guides the pushrod into the channel of the brachytherapy needle. The physician then slowly withdraws the brachytherapy needle while holding the pushrod in place. The seeds are pushed out of the needle and remain in a row inside the afflicted tissue. Multiple rows of seeds and spacers are commonly used to treat an area of tissue. Each position in a row requires a different cartridge preloaded to match the treatment plan parameters, requiring the medical staff to handle a different cartridge for each needle used.

One technique involves placing all of the radioactive seeds in a cartridge and manually injecting the seeds in the patient during a treatment. The spacing of the seeds is achieved by withdrawing the needle and injecting the seeds at spaced intervals as the needle is withdrawn. The spacing of the seeds is achieved manually without the benefit of any spacers.

Another technique exists for ensuring proper seed placement and distribution. The radioactive seeds are coupled to form a chain. The manufacturer provides the physician with assembled chains of ten seeds separated by standard spacing. Each chain arrives in a shielded package. The physician removes the chain from the shielded packaging. The physician cuts the chain to match the prescribed treatment plan. Each cut chain is then loaded into an individual brachytherapy needle. The brachytherapy needle inserts into the afflicted tissue. The physician guides the pushrod into the channel of the brachytherapy needle. The physician then slowly withdraws the brachytherapy needle while the holding the pushrod in place. The seed chain is pushed out of the needle and remains in the afflicted tissue. Multiple chains of seeds are used to treat an area of tissue. Each chain must be implanted individually in a different location of the tissue. The physician spends additional time manipulating each individual chain increasing exposure time to the radioactive seeds.

SUMMARY

An apparatus and method for administering a dose in brachytherapy comprising a handheld housing having a holder containing a dose of radioactive seeds adapted for use in a brachytherapy treatment and a display for observing information about the dose and viewing the dose or components of the dose. The display identifies and provides information about the dose and a component of a dose. A port provides access to the dose for assay. The display provides a visual display of the dose and components of the dose. A dose is loaded directly into a holder in the housing, needles are coupled to the housing and the dose is injected into the needle from the housing.

BRIEF DESCRIPTION OF THE DRAWINGS

FIG. 1 is an example of a needle-loading plan;

DETAILED DESCRIPTION

In the administration of a brachytherapy treatment the administration of a dose of radioactive seeds is performed in accordance with a treatment plan prepared by a physician for a patient. The treatment plan represents the desired distribution pattern for a plurality of radioactive seeds in the afflicted tissue. The physician employs medical tools such as ultrasound imaging, computerized axial tomography ("CAT") scans, and X-ray imaging in concert with dose-planning computer software programs for evaluating the medical condition of the patient. Each patient's tissue varies in size, shape, and location. The present stage of cancer in the afflicted tissue may also vary.

The treatment plan references a template corresponding to the patient's afflicted tissue. This allows the physician to determine ideal implant locations and indicate them on the template. Each implant location is denoted on the template with a figure, along with information regarding the depth of the needle and the quantity of seeds for that specific implant location. The implant locations are also numbered for reference before and during the operation. The physician compiles the information from the template to form a chart listing each needle and the desired location, retraction depth, and quantity of implant seeds for each needle. Another chart illustrating the seed and spacer layout in each individual needle is also prepared. The physician uses this information in the preparation of a brachytherapy treatment device and during the operation.

An example needle-loading table 102 of FIG. 1 comprises columns of data correlating a needle number 104, a needle retraction 106, a needle hole location 108, and a quantity of seeds 110. A typical procedure requires approximately twenty needles. The needle retraction 106 is the distance the needle should be withdrawn from the innermost point of the tissue. The hole location 108 designates the implant location in the afflicted tissue. The needle-loading table 102 also lists the quantity of seeds 110 to be implanted in each hole.

Figure 2:
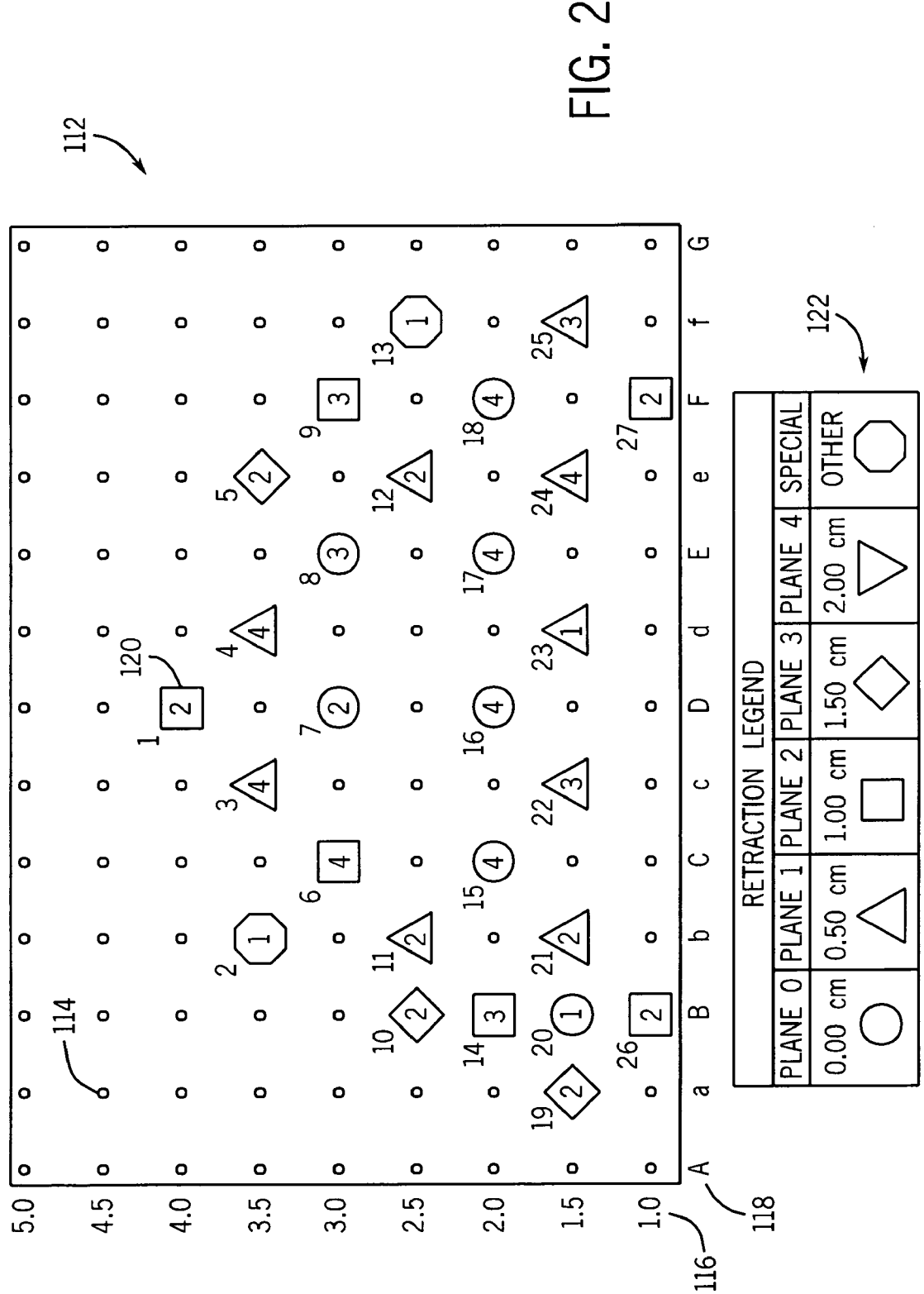
FIG. 2 is a graphical representation of a needle placement in a template.

A chart 112 illustrating a graphical representation of the needle placement in a template is shown in FIG. 2. A scale 116 along the y-axis and a scale 118 along the x-axis define a specific needle hole position 114. A legend 122 correlates each geometric figure at the hole location 114 with a given retraction depth. A superscript with each geometric figure provides the needle number 104, and the number of seeds 110 contained in each needle 104 is within the geometric figure.

Figure 3:
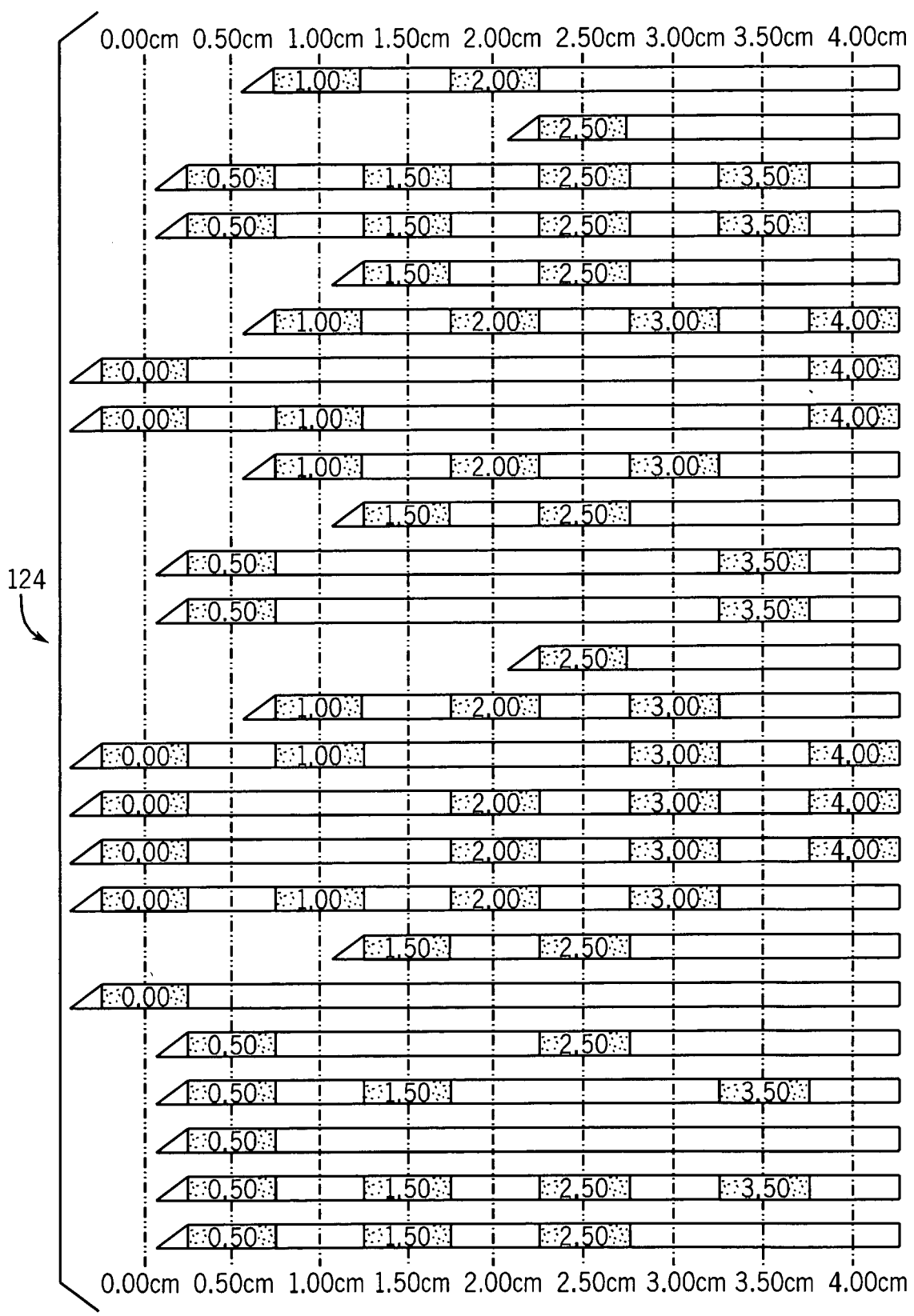
FIG. 3 is a chart illustrating seeds in each corresponding needle.
Figure 4:
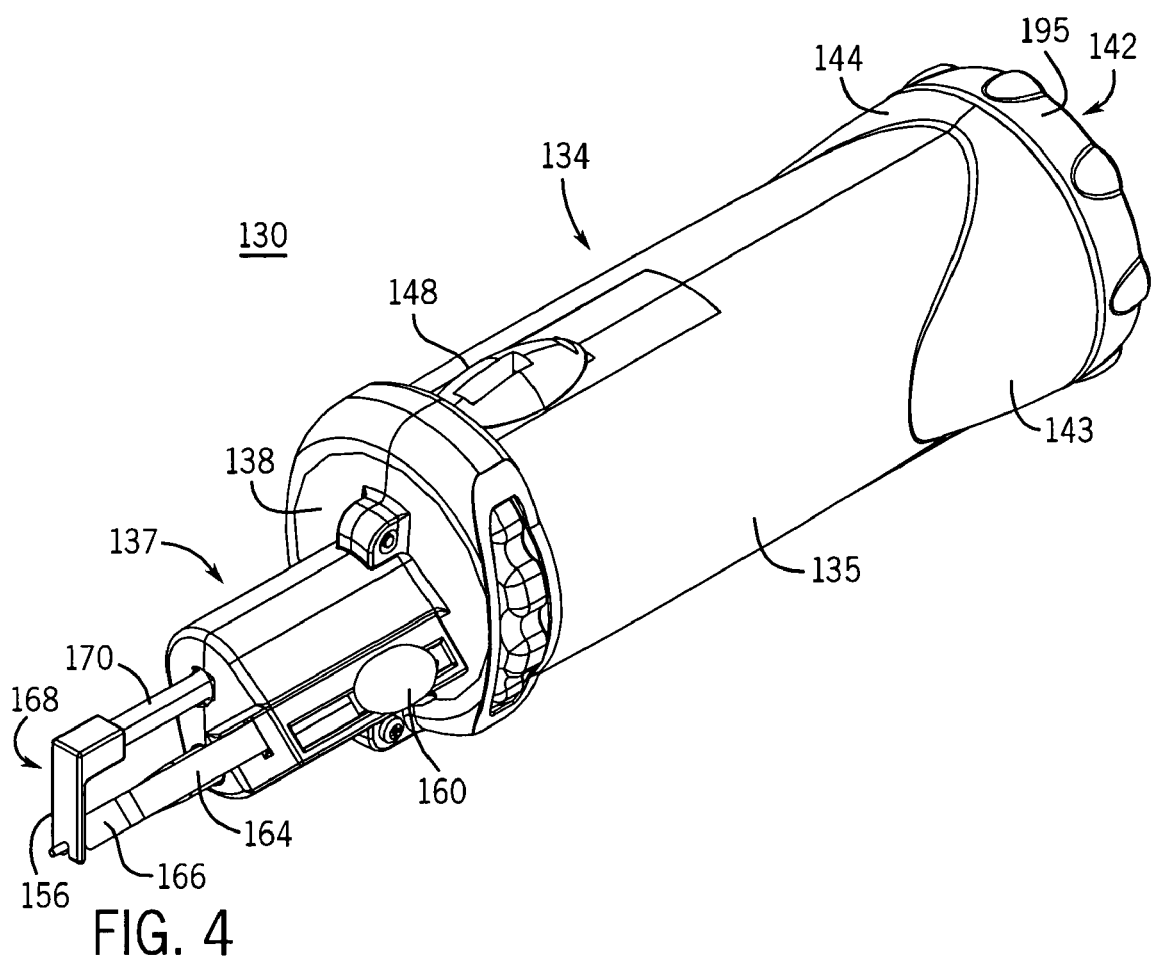
FIG. 4 is a is a perspective view of an apparatus in accordance with an example of the invention.
Figure 7:
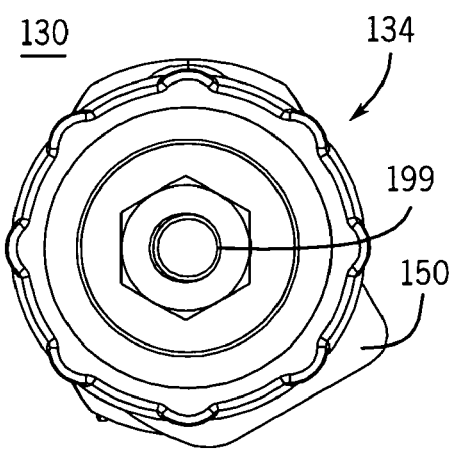
FIG. 7 is a is a rear view of an apparatus in accordance with an example of the invention.
Figure 8:
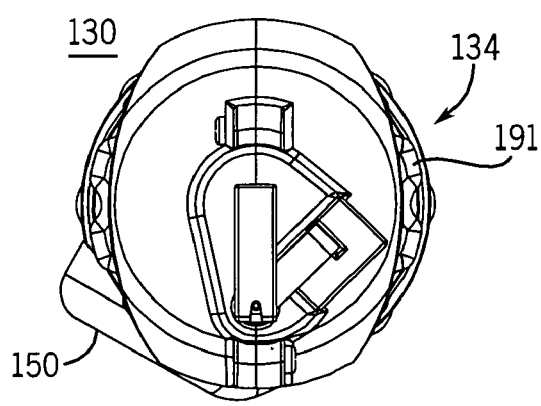
FIG. 8 is a front view of an apparatus in accordance with an example of the invention.

A chart 124 illustrating the seeds in each corresponding needle is shown in FIG. 3. A scale along the needle illustration represents the retraction depth. The pharmacist or physician employs the chart 124 for laying out the proper seed dosage prior to the operation. The physician employs non-radioactive spacers to maintain the distances between the seeds. Specially loaded needles are denoted on the correlating table with a small black circle next to the needle number. A special loaded needle is one that requires multiple adjacent spacers or spacing of non-standard lengths.

Referring to FIGS. 4 through 12, an apparatus 130 is shown in accordance with an example of the invention comprising a housing 134 having two mating sections 135 and 136, a nose 137 extending from a first end 138 of the housing 134. A guide 140 is located at a second end 142 of the housing 134. The guide 140 comprises a pair of tapered raised portions 143 and 144 extending toward the first end 138 of the housing 134. The guide 140 assists in controlling the apparatus 130 with either a right hand or a left hand during the operation of the apparatus 130 by the physician.

The housing 134 is comprised of radiation shielding material. For example, the housing 134 may comprise stainless steel or lead. In another example, the housing 134 comprises a "loaded" plastic. The "loaded" plastic is a plastic that is mixed with materials with radiation shielding characteristics, yielding a plastic with similar radiation shielding characteristics, such as the Ecomass compounds available from PolyOne Corporation (www.ecomass.com). In one example, the housing 134 comprises 0.100" thick "loaded" plastic made up of nylon 12 mixed with approximately 33% by volume bismuth subcarbonate.

In another example of the invention, the housing 134 may further comprise a plurality of apertures (not shown) connected to the radioactive seeds. To avoid radioactive exposure the apertures do not provide a direct line of sight to the radioactive seeds. The radioactive seeds may then be exposed to a sterilizing while in the housing 134. The sterilizing agent may be gamma radiation, pressurized steam, ethylene oxide gas or vaporized hydrogen peroxide.

A display 148 is located on the surface of the housing 134. The display 148 comprises: a first subcomponent display 149, such as a slide button coupled with the housing 134, that provides information about the dose contained within the housing 134; a port to assay a sample of the dose; and a second subcomponent 150 to view the dose or all of the components of the dose, including the dose or component of the dose next to be ejected from the apparatus 130.

A terminating member 154 has a base member 155, located within the housing 134, and a stalk 156 extending outward of the nose 137. An engaging member 158 is connected to the nose 137. The engaging member 158 is operated by an actuator 160. The engaging member 158 has an extendable member 164 that is moved outwardly and inwardly of the nose 137 by the operation of the actuator 160. As will be explained, an end 166 of the extendable member 164 engages a needle and moves the needle into a coupled relationship with the stalk 156.

Figure 6:
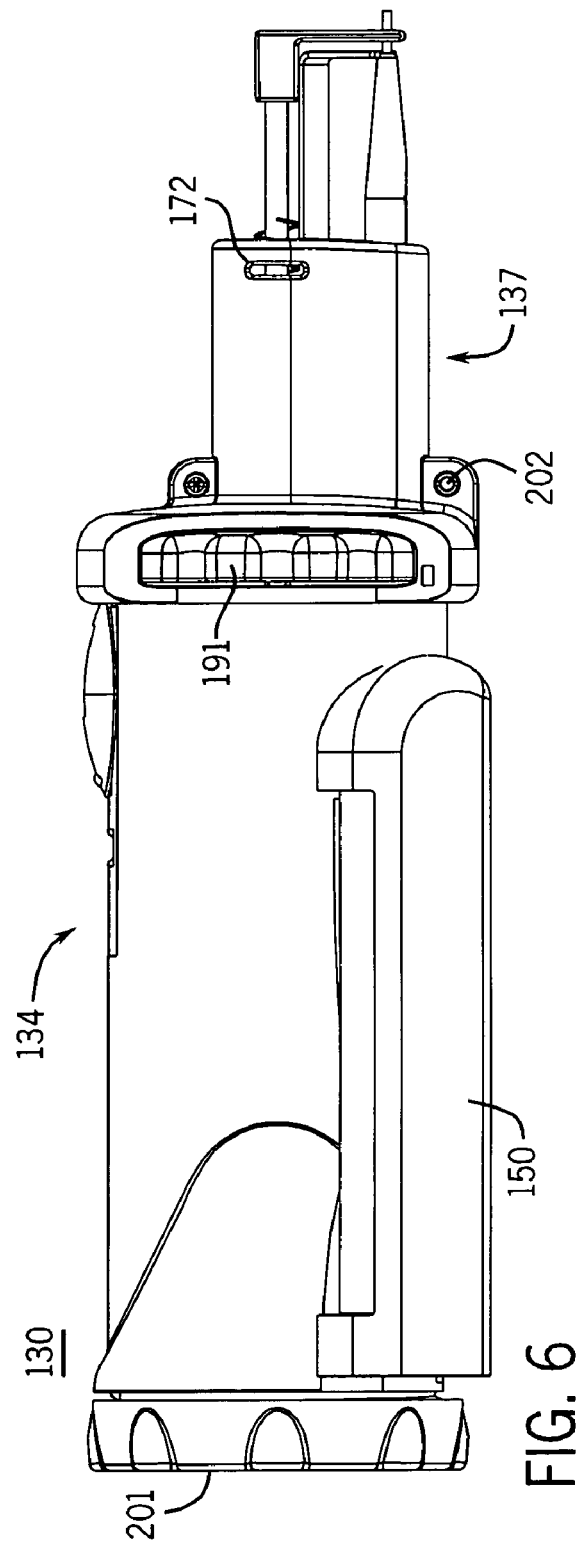
FIG. 6 is a side view of an apparatus in accordance with an example of the invention.

An adjustable indicator 168 has a body portion 169 located within the housing 134. A collar 173 abuts the base member 155 of the terminating member 154. A spring biased extension member 170 extends outwardly of the nose 137. As shown in FIG. 6, a stop member 172 restrains the spring biased extension member 170 in a compressed position. The extension member 170 has a forked end 174 that is positioned adjacent to the stalk 156. Those skilled in the art will be familiar with stop structures that may be used as stop members to hold a member from moving against a spring bias.

In a fully extended or unrestrained mode, the extension member 170 extends outwardly with the forked end 174 in contact with a needle grid to make a measurement to position the dose in the correct location in tissue. In one example of the invention, the physician knows the retraction distance and moves the housing 134 toward or away from the needle grid until the correct retraction measurement is indicated usually in centimeters on the adjustable indicator 168. The physician may then begin the administration of the dose in the tissue.

In another example of the invention, the extension member 170 of the adjustable indicator is manually extended outwardly at fixed intervals, for example, in one-half centimeter intervals. The physician then manually extends and fixes the extension member 170 to the required retracted distance for the dose, places the forked end 174 in contact with the needle grid and administers the dose.

Figure 13:
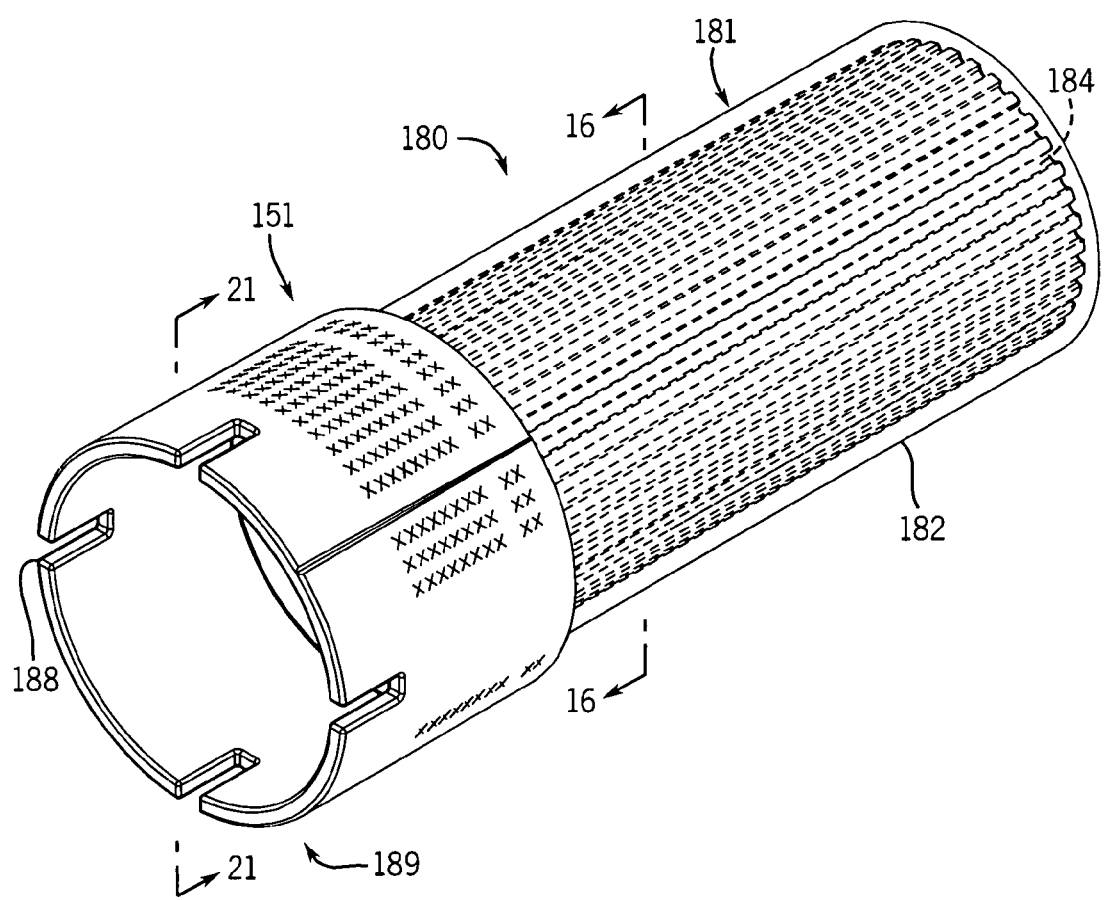
FIG. 13 is a view of a holder of the apparatus in accordance with an example of the invention.
Figure 16:
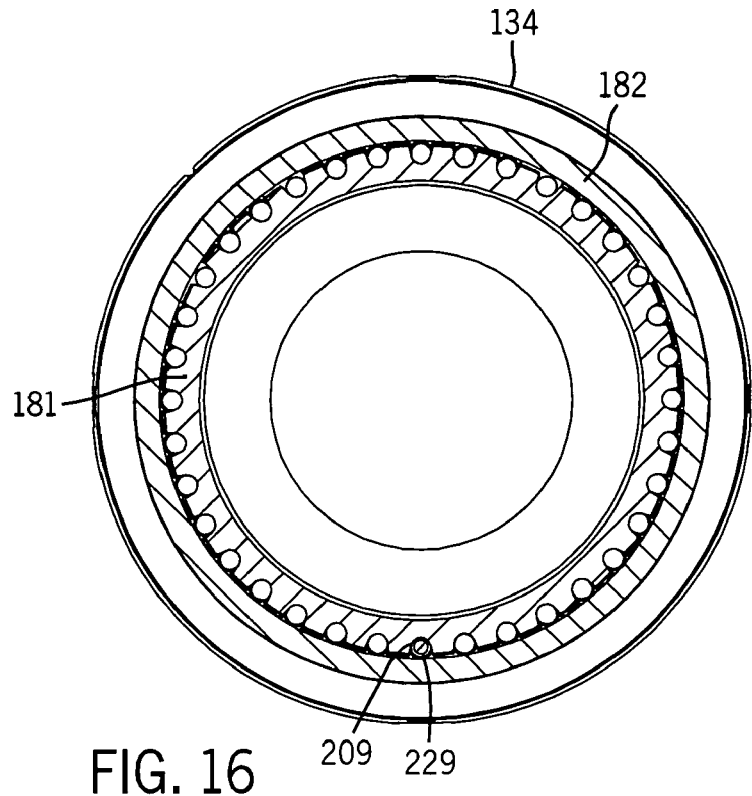
FIG. 16 is a section view along 16–16' shown in FIG. 13 of the apparatus in accordance with an example of the invention.
Figure 17:
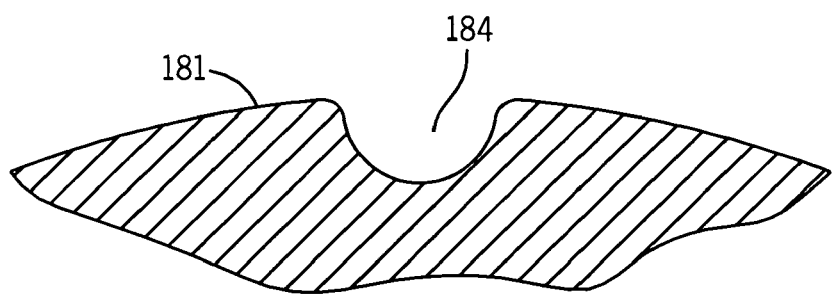
FIGS. 17 and 18 are cross sections of grooves of a cylinder of the apparatus in accordance with an example of the invention.
Figure 18:
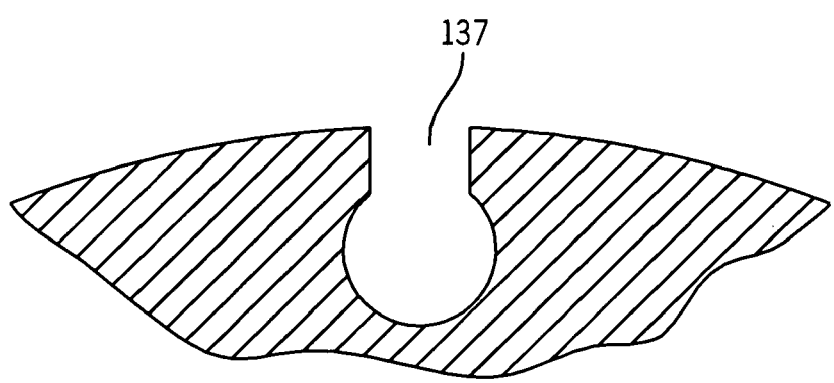

A holder 180 as shown in FIG. 13 has a cylinder 181 and a barrel 183 connected to an end of the cylinder 181. The cylinder 181 has parallel grooves 184. A cross-section of the cylinder 181 is shown in FIG. 16. Referring to FIG. 17, the grooves 184 have a U-shaped cross-section. In another example, shown in FIG. 18, each of the grooves has a semi-circular cross-section and a channel 187 connecting the groove to the surface of the cylinder 181.

In one example of the invention as shown in FIG. 16, the cylinder 181 has 36 grooves. A polycarbonate sleeve 182 surrounds the cylinder 181. The polycarbonate sleeve 182 serves to retain the seeds and spacers in the grooves 184. In a treatment plan, the grooves 184 in the cylinder 181 may be occupied with the dose or a plurality of component doses of the treatment plan. The component doses may each include a combination of radioactive discrete seeds and spacers, or stranded doses comprised of a continuous strand of radioactive seeds and spacers. The remaining grooves may be left unoccupied or used for a dose of radioactive seeds not included in the treatment plan to be used at the physician's discretion.

Referring additionally to FIG. 13, the barrel 183 has slots 188 extending inwardly from an end 189 of the barrel 183. An indexing wheel 190 is connected to the holder 180 having a knurled edge 191 projecting beyond an exterior surface of the housing 134. The indexing wheel 190 has projections 192 that couple with the slots 188 in the barrel 183.

An end cap 193 has an annular end 196 that is slidably coupled with an inner surface 197 of an end of the cylinder 181. When the holder 180 is coupled within the housing 134, the indexing wheel 190 engages and rotates the barrel 183 rotating the holder 180 and the cylinder 181 with the end of the cylinder 181 rotating about the annular end 196 of the end cap 193.

Figure 11:
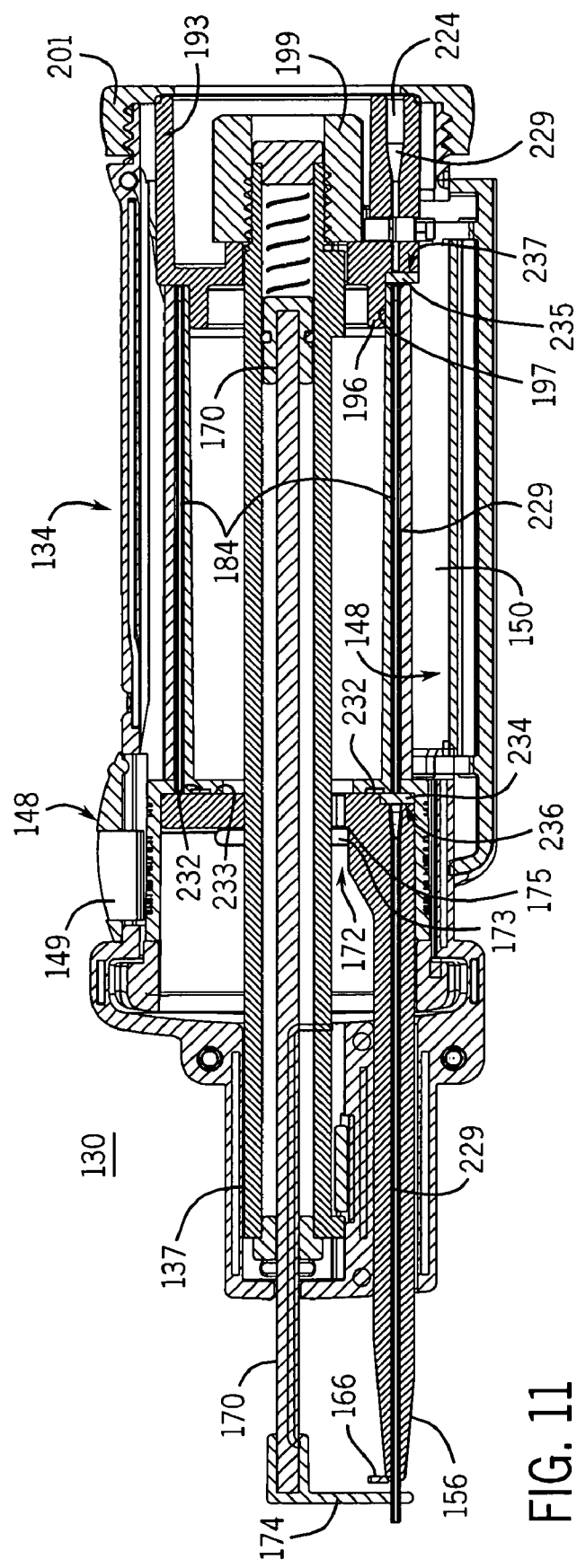
FIG. 11 is a section view along 11–11' shown in FIG. 5 of an apparatus in accordance with an example of the invention.

A threaded connector 199 holds the end cap 193 abutted to the housing 134. The end cap 193 is held in the abutting relationship with the housing 134 because of the threaded connection of the end cap 193 with a threaded portion 200 of the adjustable indicator 168. Referring to FIG. 11, the collar 173 of the adjustable indicator 168 abuts the base 155 (see FIG. 12) and restrains the adjustable indicator 168 and an opposed end at an interface 175.

An annular threaded connector 201 and fasteners 202 connect the two mating sections 135 and 136 of the housing 134.

As shown in FIG. 13, the cylinder 181 includes a plurality of parallel grooves 184. In one example of the invention, the grooves 184 are in the surface of the cylinder 181. In one example of the invention, the dose in accordance with the treatment plan comprises a plurality of component doses and each groove of the parallel grooves 184 may contain one of the plurality of component doses.

Referring to FIG. 13, a surface 151 of the barrel 183 includes information about each of the plurality of component doses that corresponds to the treatment plan. The information may include a specific number or identity of the component dose, the spatial rectangular or three dimensional coordinates of the dose, and the retraction distance.

Figure 14:
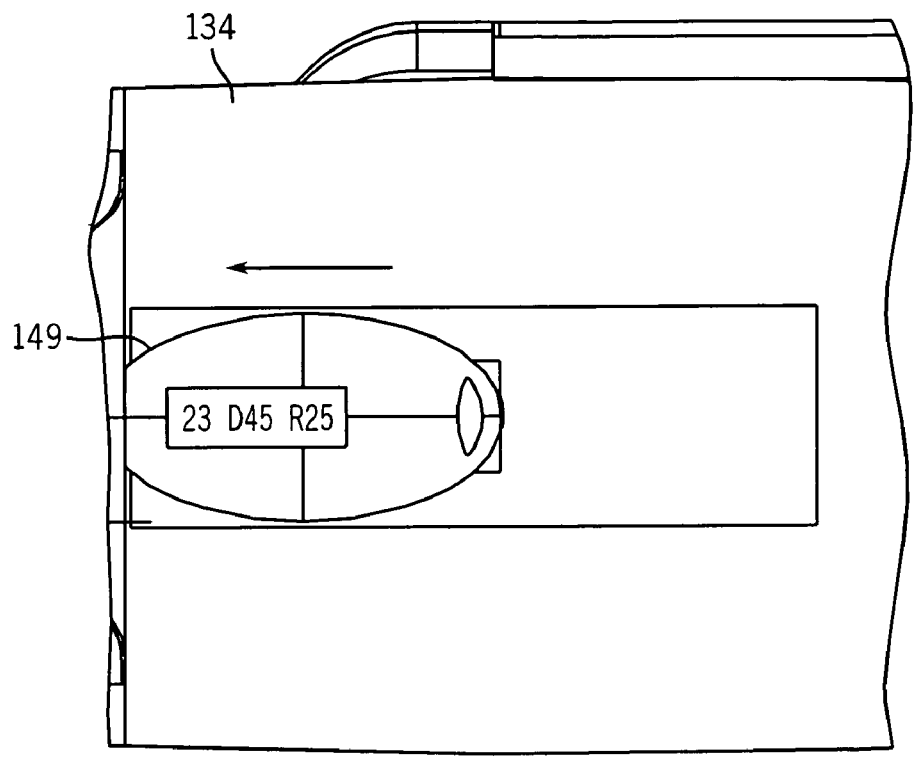
FIGS. 14 and 15 are top views of a display of the apparatus in accordance with an example of the invention.

In FIG. 14, the first subcomponent display 149 is shown positioned toward the first end 138 of the housing 134, and the information shown at the first subcomponent display 150 is 23, D4.5, R 2.5, where 23 is the number or identity of one of the plurality of the component doses, D4.5 represents the spatial coordinates on the needle grid and 2.5 is the retraction distance usually specified in centimeters.

Figure 15:
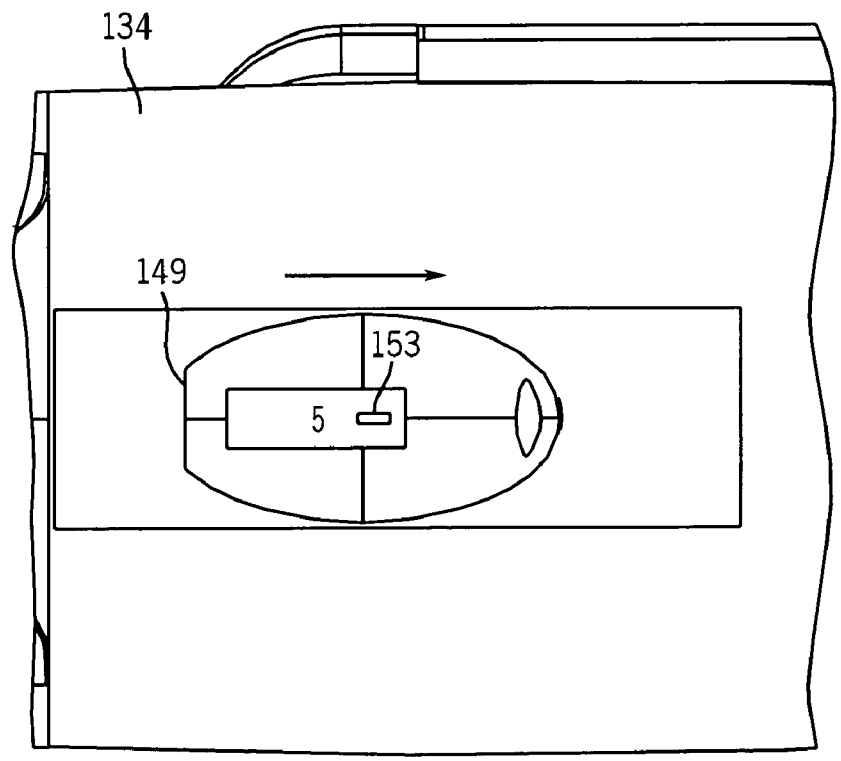

In FIG. 15, the first subcomponent 149 is shown positioned toward the second end 142 of the housing 134. In this position, a sample of the dose identified by dose number may be observed for assay at assay port 153. In one example of the invention, the identity of the assay dose is given. For example if the first subcomponent display 149 indicates that dose or component of a dose 23 is next to be ejected from the housing, then the assay dose is positioned one hundred and eighty degrees opposed on the cylinder 181 and is dose number 5. That is, if the display shows a next dose to be given adjustable indicator, then the information is located 180 degrees from the next dose (see FIGS. 4 and 13.

The first subcomponent display 149 is coupled to the housing 134 and restrained in position by means known to those in the art. For example, detents and raised protuberances on the housing 134 and the display 150 may cooperate to temporarily restrain the display 149 in a position.

Figure 5:
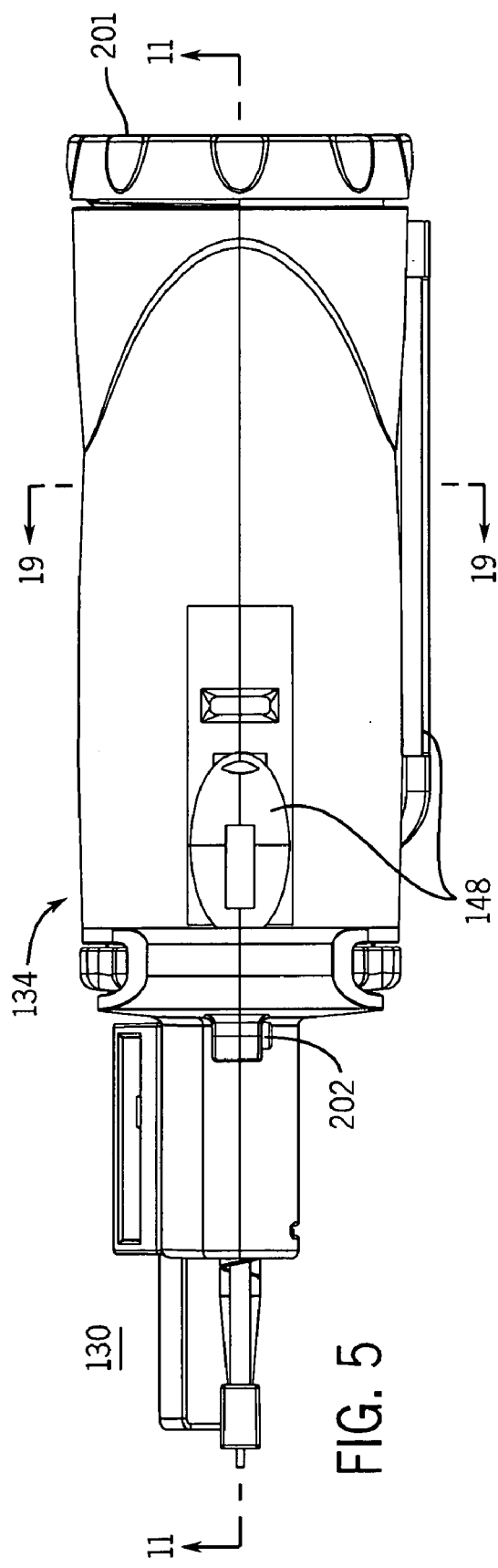
FIG. 5 is a top view of an apparatus in accordance with an example of the invention.
Figure 19:
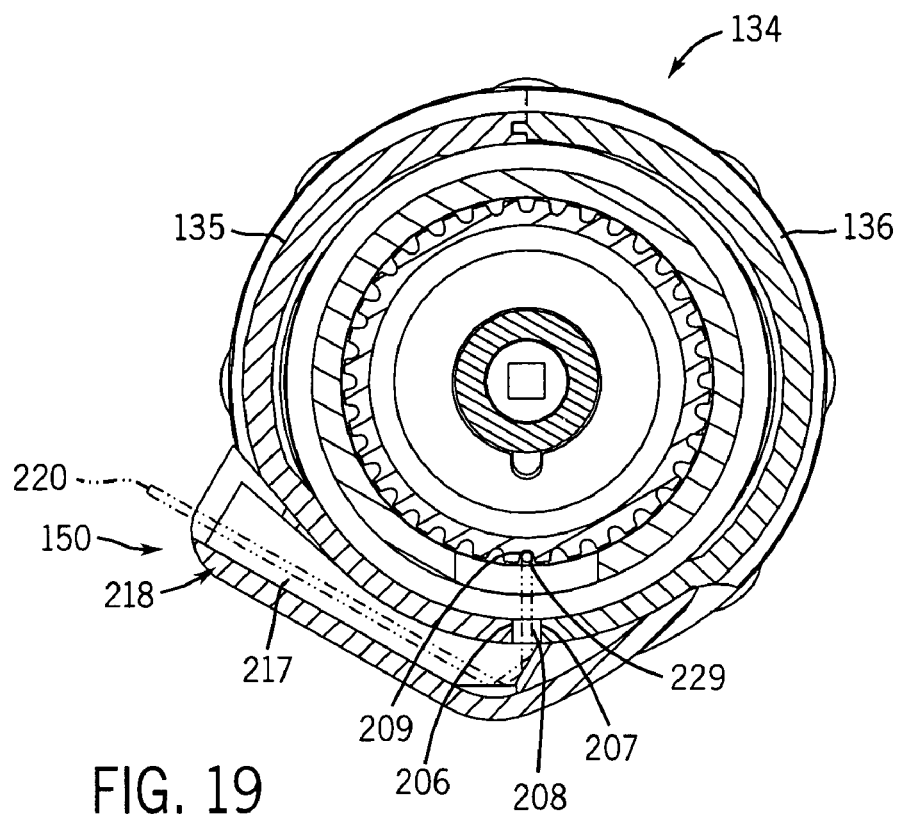
FIG. 19 is a cross sectional view along 19–19' shown FIG. 5 of the apparatus in accordance with an example of the invention.

Referring to FIGS. 5 and 6, the second subcomponent display 150 for observing the dose is located along the housing 134. Referring to FIG. 19, the mating sections 135 and 136 of the housing 134 have a spaced relationship along adjacent perimeter edges 206 and 207 defining a slot 208. Referring to FIGS. 16 and 19, one dose of the plurality of component doses would be located in a groove 209 aligned with the slot 208 in a spaced relationship. The one dose in the groove 209 is the next dose to be ejected from the apparatus 130. The groove 209 is aligned with the pathway 229.

In one example, shown in FIG. 19, the second subcomponent display 150 comprises a hood 216 extending outwardly from the housing 134 for containing an element 217 that allows an indirect view of the one dose without radioactive exposure. The element 217 may be constructed, for example, of a light pipe, prism or a combination of mirrors. Those skilled in the art are aware of designs that will permit indirect viewing of the one dose without radioactive exposure. The one dose is observed at an end 218 of the hood 216. The path of sight 220 is shown from the end of the hood 218 through the element 217, the slot 208 to the dose and all components of the dose in the groove in the cylinder 181.

Figure 20:
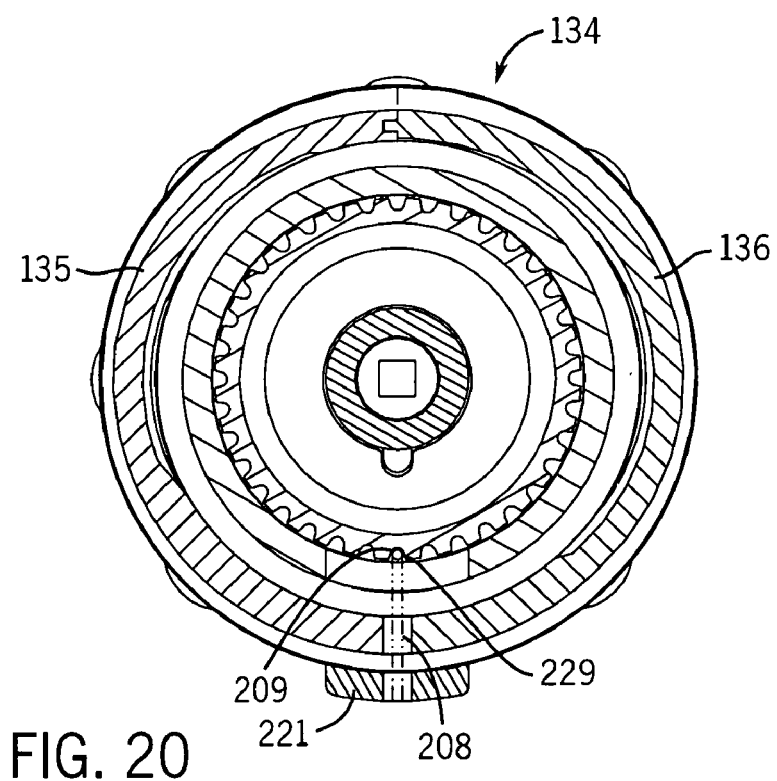
FIG. 20 is another example of the cross section of FIG. 18 of an apparatus in accordance with another example of the invention.

Referring to FIG. 20, in another example, the dose and all components of the dose can be observed directly through leaded glass or plastic 221.

The end cap 193 has a channel 224 that is aligned with a channel 229 in the stalk 156. Each of the plurality of grooves 184 are selectively rotatably positioned in an alignment with the channel 224 of the end cap 193 and the channel 229 of the stalk 156. This alignment is shown in FIG. 11 as an aligned pathway 229.

Figure 21:
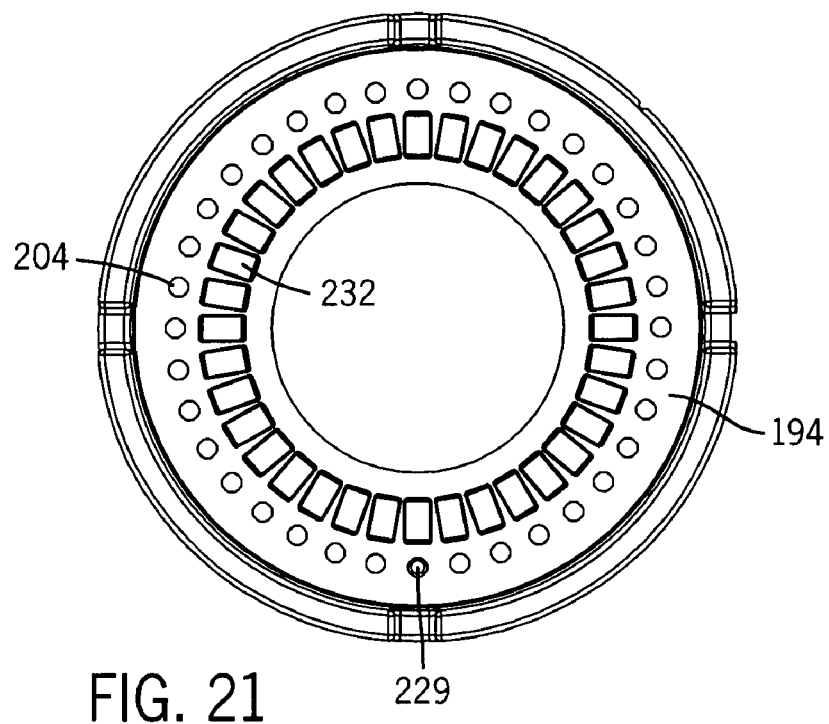
FIG. 21 is a front view along the line 21–21' as shown in FIG. 13 of an apparatus in accordance with an example of the invention.
Figure 22:
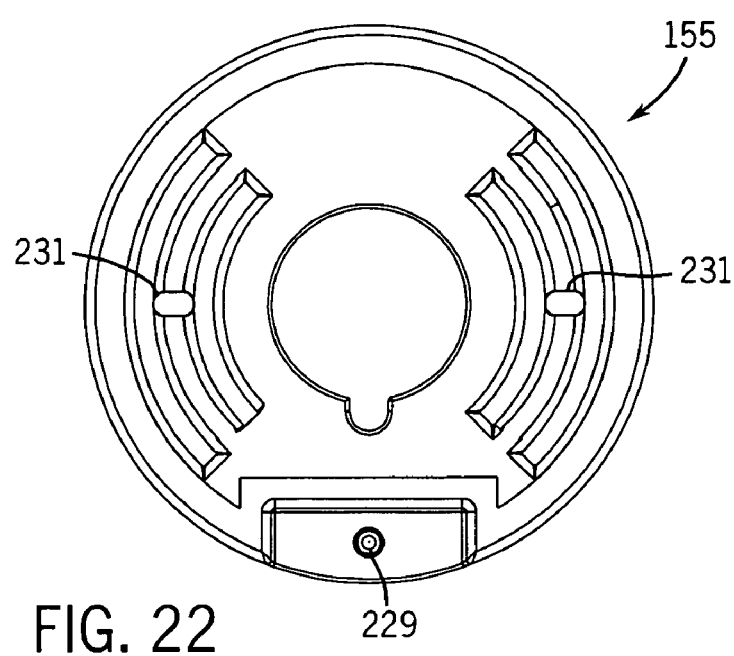
FIG. 22 is a view along the line 22–22' as shown in FIG. 12 of an apparatus in accordance with an example of the invention.
Figure 23:
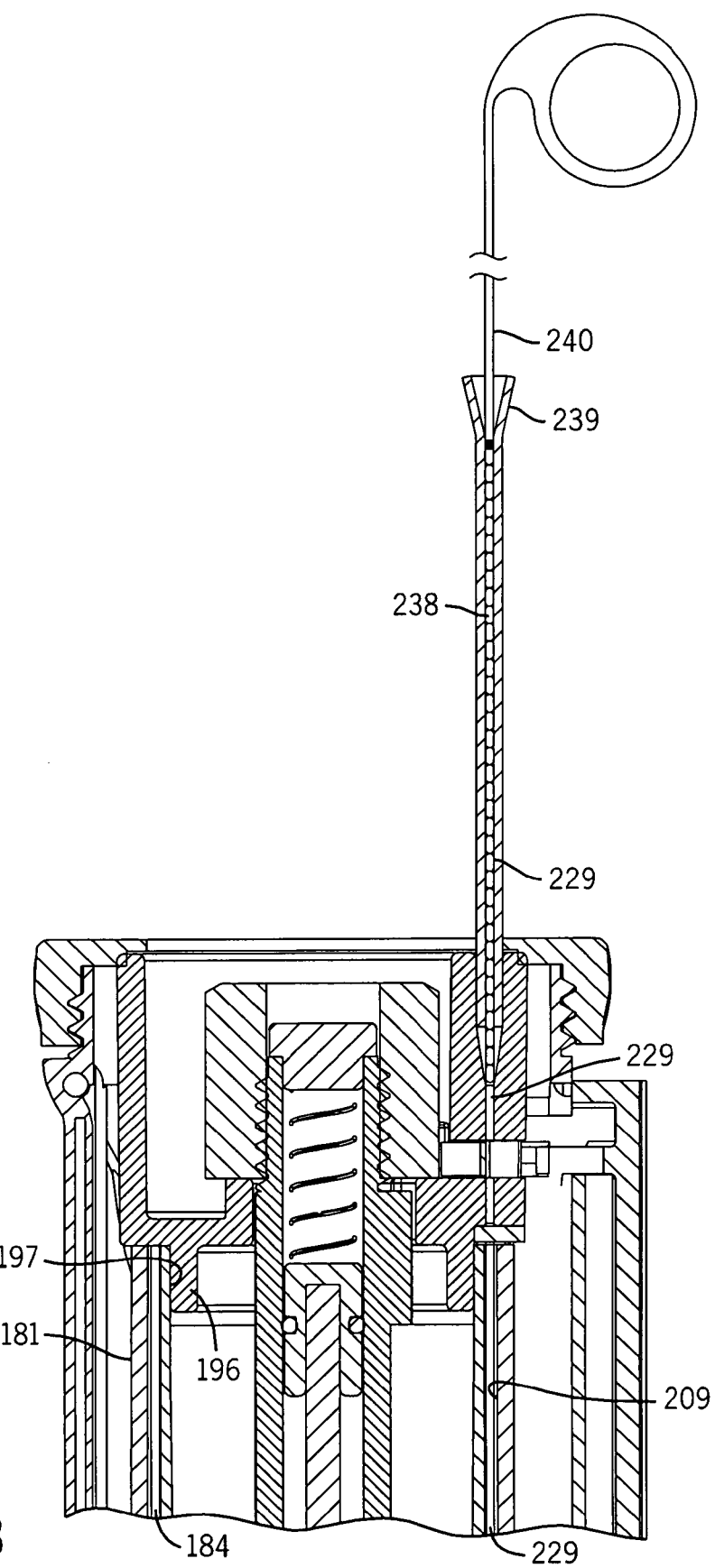
FIG. 23 is a partial view of loading the apparatus in accordance with an example of the invention.

The rotation is secured by the lock member 230, which comprises a combination of the base 155 and the annular surface 194 shown in FIGS. 21 and 22. The selective positioning and engagement of projections 231 of the base 155 with slots 232 in the surface 194 results in an engaged interface at 233 as shown in FIG. 11. The projections 231 are received by the slots 232 and provide resistance to an undesired rotation of the holder 180 and cylinder 181. By the pre-selected placement and location of the projections 231 and the slots 232, each of the grooves 184 is selectively aligned in the pathway 229 when the dose or one of a plurality of doses is loaded in or ejected from a selected one of the grooves 184 in the cylinder 181. Apertures 204 in the surface 194 are aligned with the grooves 184 in the cylinder 181 and selectively with the pathway 229. The groove 209 is only an example as all of the grooves 184 may be selected as groove 209 for alignment with pathway 229 to receive or eject a dose or one of a plurality of doses.

A pair of gates or baffles 234 and 235 are located at an interface 236 of the stalk 156 and each of an aligned groove and at an interface 237 of the end cap 193 and the aligned groove 209, respectively.

Referring to FIG. 21, the dose of a treatment plan or a dose adapted for a subsequent treatment plan developed by a physician is loaded from the end cap 193. The individual or stranded seeds or stranded linked seeds 238 and any spacers are positioned in a loader 239.

A stylus or tool 240 is applied to an end of the dose, and the dose is advanced through the channel 224 in the end cap 193 through the gate or baffle 235 and into an aligned groove in the cylinder 181. The dose and the stylus 240 pass through the gate or baffle 235, and after the dose is loaded in the groove, the stylus 240 is retracted and the gate or baffle 235 self seals and restrains the dose within the groove. A selected number of the grooves may be loaded. After one of the grooves 184 is filed with a dose, the cylinder 181 is rotated to the next selected groove that is selected to be filled with a dose. In one example, the gates or baffles 234 and 235 are comprised of an elastomer.

Figure 9:
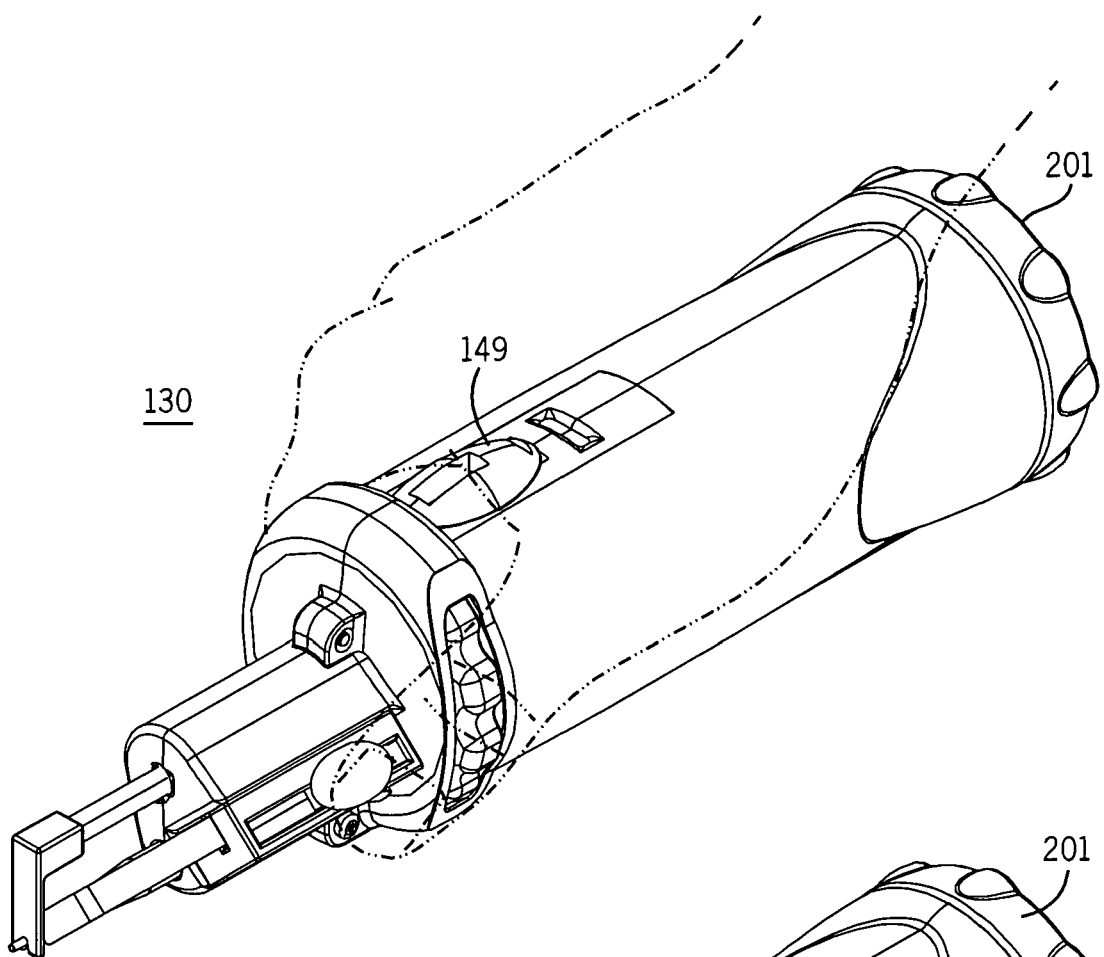
FIGS. 9 and 10 are a perspective views showing phantom hands with an apparatus in accordance with an example the invention.
Figure 10:
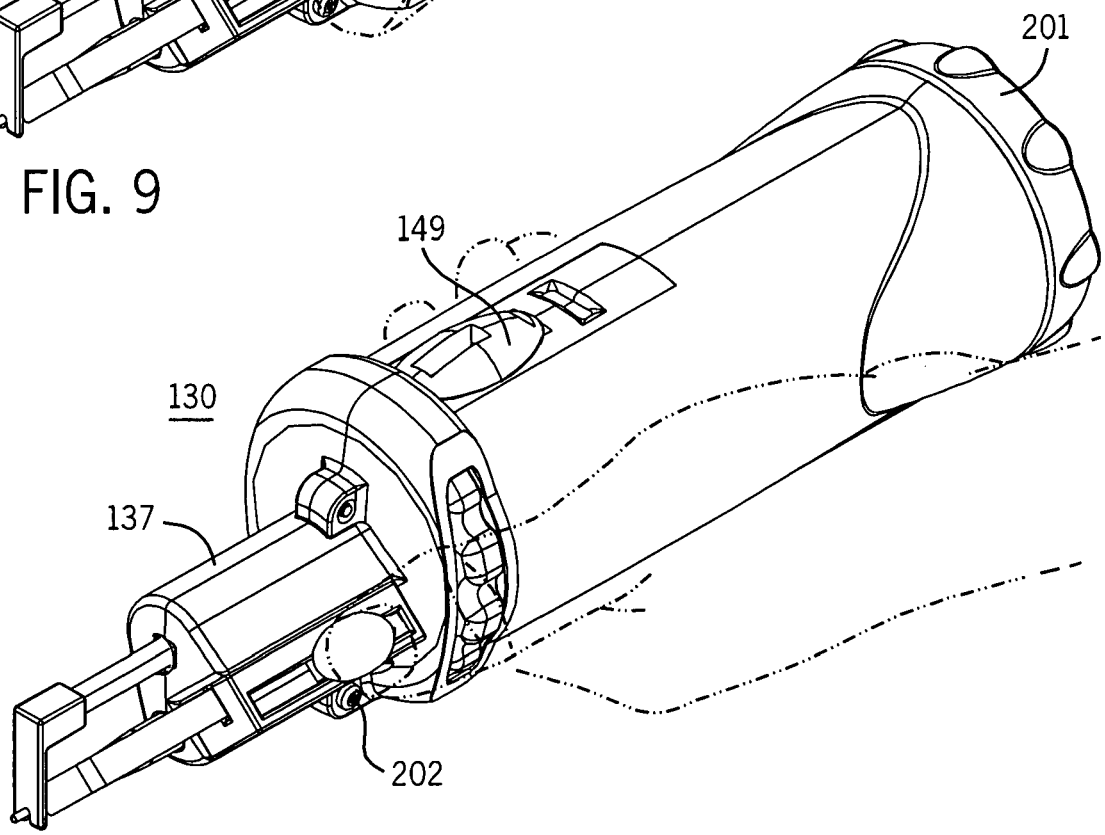
Figure 12:
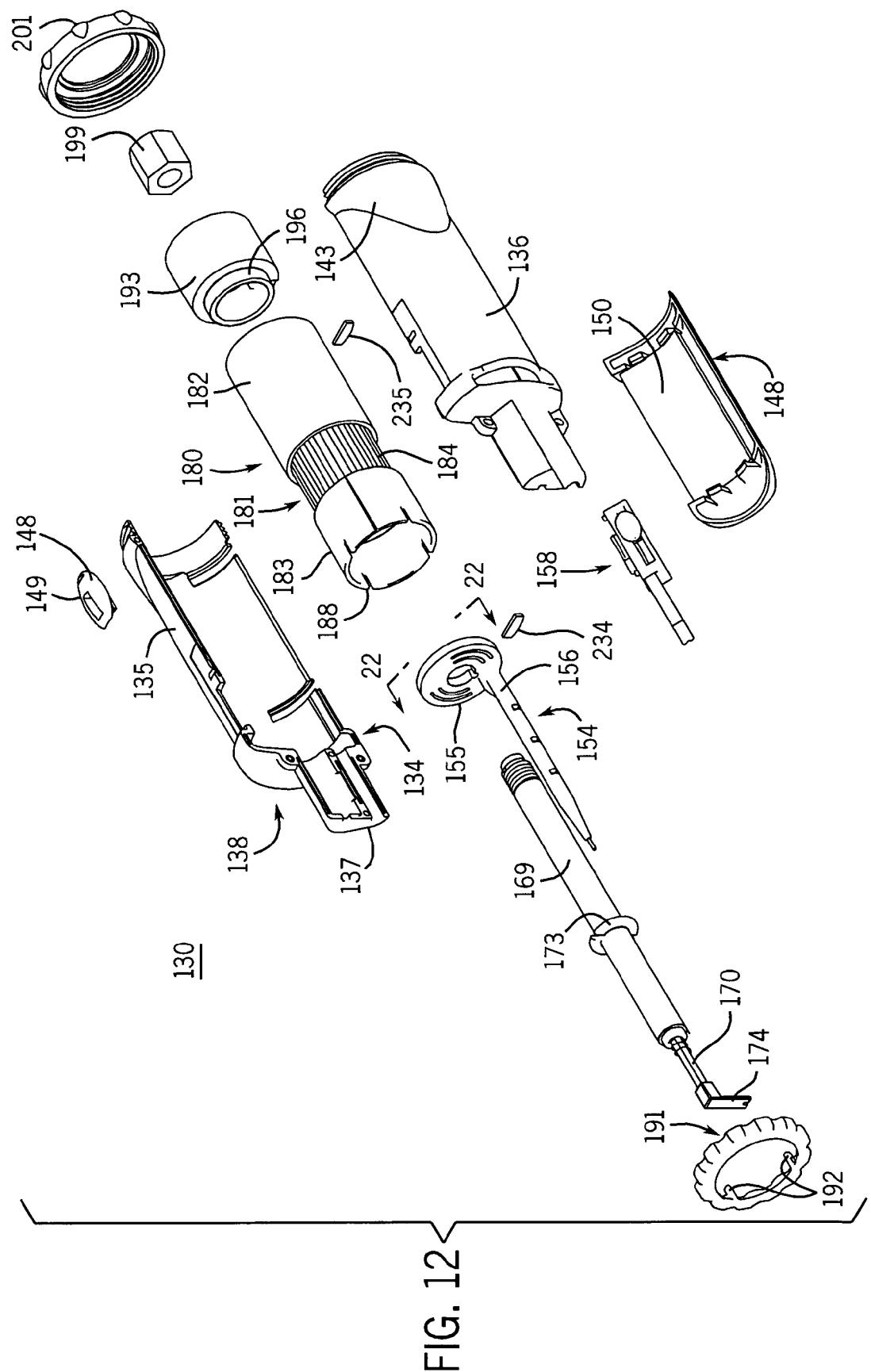
FIG. 12 is an exploded view of an apparatus in accordance with an example of the invention.

In using the apparatus 130 for loading needles and for loading needles in a needle grid with the needles in place in the tissue, the stalk 156 of the termination member 154 is first coupled with a hub 241 of a needle. Referring to FIGS. 9 and 10, the housing 132 is shown grasped by the left hand or right hand, respectively, with the bottom of the hand position in the guide 140 of the housing 134 for control by the operator of the apparatus 130. A thumb is shown positioned on the actuator 160 of the engaging member 158. The actuator 160 shown the FIG. 12 is shown in the retracted position.

Figure 24:
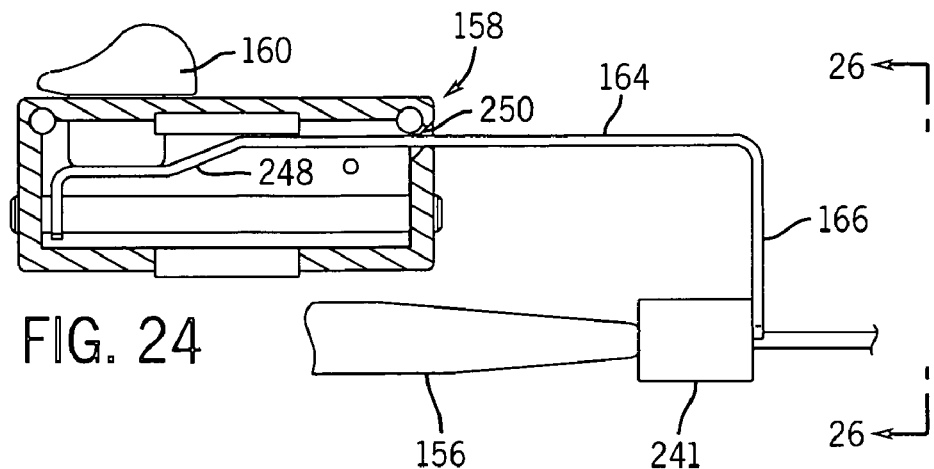
FIGS. 24 and 25 depict side views of an engaging member of an apparatus in accordance with the invention.
Figure 25:
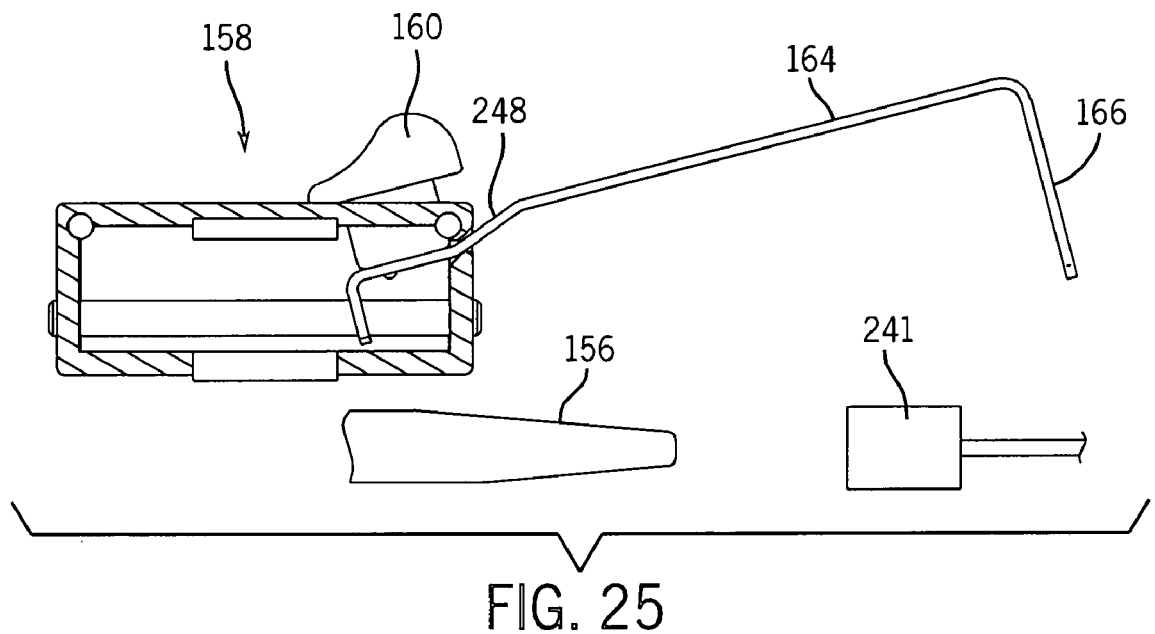
Figure 26:
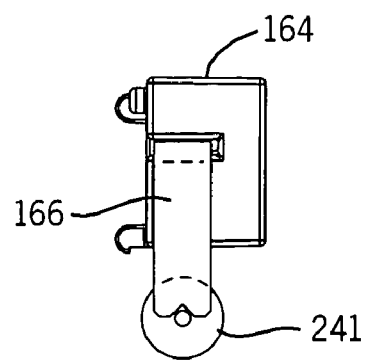
FIG. 26 is a front view along the line 26–26' shown in FIG. 24 of an apparatus in accordance with an example of the invention.

Referring to FIG. 24, the actuator 160 is shown in the retracted position with the extendable member 164 retracted in the nose 137 of the housing 134. Referring to FIG. 25, the actuator 160 extends outwardly of the nose 137. In the extended position, a sloped segment 248 of the extendable member 164 passes through an angled slot 250 that moves the extendable member 164 away from the retracted position of the extendable member 164.

In engaging or bringing the stalk 156 into a coupled relationship with the hub 241 of a needle, the actuator 160 is moved outwardly of the nose 137 with the forked end 174 positioned above the needle and behind the hub 241 of the needle. When the actuator 160 is retracted, the forked end 174 engages the needle behind the hub 241 and as retraction is continued the needle is engaged or brought into a coupled relationship with the stalk 156.

After the needle is engaged or brought into coupled relationship with the stalk 156, the stylus 240 is inserted through the pathway 229. This is done by inserting the stylus 240 into the channel 224 of the end cap 193 and advancing it through the gate or baffle 235 and though the aligned groove 209 in the cylinder 181, and continuing on to move the dose out of the groove and through an aligned one of the apertures 204 and through the gate or baffle 234 and through the channel 228 in the stalk 156 and then into the needle.

In an example of an application of this invention in medical practice, an examination of the patient is conducted using various medical methods to determine the treatment plan. The seed placement template 102, needle loading table 112, and needle loading chart 124 are prepared according to the physician's plan and an apparatus 130 in accordance with the invention is ordered to enable the physician to implement the treatment plan.

A dose including radioactive seeds are loaded into grooves 184 on the seed cylinder 181 as prescribed in the treatment plan. Each of the grooves 184 receives a set of radioactive seeds which are destined for a particular brachytherapy needle and particular locations in the patient's prostate. Depending on the physician's plan, some of the grooves 184 may remain empty. The physician may also desire to have extra seeds placed into unused grooves 184 for "spares" to be available if needed during the treatment. The apparatus 130 may then be sterilized prior to shipment to the physician.

When the physician receives the apparatus 130 loaded with a dose in accordance with the treatment plan, the physician may: (1) assay the radioactivity of specific seeds in order to verify the correct needle load in accordance with recognized standards, and (2) visually inspect the complete dose at the display 150 by rotating the cylinder 181 and inspecting the dose loaded in each of the grooves 184.

The treatment plan in accordance with another example of an embodiment of the invention comprises the treatment of tissue with radioactive seeds with the determination of the quantity and location of the treatment made independent of the loading of the housing. In other words, the dose loaded in the housing is a combination of radioactive seeds and any spacers that would be able to provide the treatment necessary for a broad number of patient applications. The physician in this situation would make the determination of where to place the dose in the tissue as require at the time of the treatment or during an examination of the patient prior to the time of the treatment.

In administering the dose, the physician attaches the brachytherapy needle to the apparatus 130 as previously described herein. The physician then inserts the brachytherapy needle into the afflicted tissue. The brachytherapy needle is withdrawn by the retraction distance 118 indicated on the treatment plan 102. The physician may attach a fixture to the operating table to help guide the brachytherapy needle into the patient.

Each implant location will have the corresponding dose within the apparatus 130. The physician selects a dose by rotating the indexing wheel 190 and observes at the display 148 information about the dose such as the identity of the dose in its associated groove. The physician operates the stylus 240 to eject the dose into the tissue with the brachytherapy needle. The physician retracts the brachytherapy needle from the tissue. The physician moves on to the next implant location. A brachytherapy needle is inserted into the patient at the next implant location. The physician then chooses the next set of seeds and uses the stylus 240 to insert them into the patient's tissue. The process is repeated until all of the seeds have been implanted. The apparatus 130 may then be reused or discarded.

In another embodiment of the method called "afterloading", the physician inserts a plurality of brachytherapy needles into the desired implant locations. Each brachytherapy needle is withdrawn by the specified retraction distance 118 as specified by the treatment plan to ensure proper dose placement. The apparatus 130 is then attached to a brachytherapy needle.

The physician selects the set of seeds for the first implant location and inserts them into the tissue using the stylus 240. The apparatus 130 is then detached from the first brachytherapy needle and attached to the second brachytherapy needle. The physician selects the dose for the second implant location and inserts them into the tissue through the brachytherapy needle using the stylus 240. After all of the seeds have been implanted the apparatus 130 is either reused or discarded.

The present invention may be embodied in other specific forms without departing from the spirit or essential characteristics. The described embodiments and examples are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. An apparatus, comprising:
   a housing;
   a holder in the housing that contains a dose of radioactive seeds corresponding to a treatment plan;
   a display for providing information for the dose according to the treatment plan;
   wherein the treatment plan comprises a plurality of radioactive seeds;
   wherein the housing comprises all of the plurality of radioactive seeds of the treatment plan;
   wherein the dose of radioactive seeds comprises a plurality of component doses;
   wherein each component dose comprises a needle load of one or more of the radioactive seeds;
   wherein the dose is ejected from the holder in the housing into one or more needles.

2. The apparatus of claim 1, wherein the dose is contained in the housing in an order corresponding to the treatment plan.

3. The apparatus of claim 1, wherein the housing allows ejection of the dose in an order corresponding to the treatment plan.

4. The apparatus of claim 1 wherein the housing allows ejection of the seeds from the housing in an order corresponding to spatial coordinates required by the treatment plan.

5. The apparatus of claim 4, wherein the treatment plan comprises a distribution pattern of the dose in a predetermined quantity of tissue.

6. The apparatus of claim 1, wherein the holder comprises a cylinder that receives the dose.

7. The apparatus of claim 6, wherein the cylinder comprises grooves in an outer surface thereof that receive the dose.

8. The apparatus of claim 7, wherein the grooves have a generally U shaped cross-section.

9. The apparatus of claim 7, wherein the grooves have a cross-section comprising a generally circular portion inwardly of the outer surface of the cylinder with a channel connecting the circular portion with the surface of the cylinder.

10. The apparatus of claim 7, further comprising a sleeve surrounding the cylinder thereby restraining the dose in the grooves of the cylinder.

11. The apparatus of claim 7, further comprising:
    a first gate at one end of the cylinder;
    a second grate at an opposed end of the cylinder; and
    wherein the first gate and the second gate restrain the dose within the grooves.

12. The apparatus of claim 11, wherein each of the first and second gates further comprises an elastomer.

13. The apparatus of claim 1, wherein the dose further comprises a plurality of component doses including at least one of discrete radioactive seeds and a continuous strand of radioactive seeds.

14. The apparatus of claim 1, wherein the information about the dose is an identity of one of the plurality of component doses.

15. The apparatus of claim 1, wherein the dose comprises a plurality of component doses and the holder comprises a cylinder having parallel grooves on a surface thereof with each groove receiving one of the plurality of component doses.

16. The apparatus of claim 15, further comprising a terminating member connected to an end of the housing, and the terminating member having a channel aligned selectively with each groove in the cylinder and adapted to be coupled to a needle.

17. The apparatus of claim 16, further comprising a wheel for rotating the cylinder for selective alignment of a selected one of the grooves with the channel in the terminating member.

18. The apparatus of claim 17, further comprising:
a barrel connected to the wheel and the cylinder and wherein the barrel includes information associated with each of the plurality of components doses;
a first display component that provides information about each of the plurality of component doses;
a second display component that discloses a one of the component doses next to be ejected from the housing; and
a lock member coupled to the wheel that secures the cylinder in a secured position for each of the plurality of component doses in association with the first display component and the second display component.

19. The apparatus of claim 17, further comprising:
first and second gates located at opposed ends of the grooves for restraining movement of the dose within the grooves; and
a stylus slidable through each gate of the first and second gates, the stylus contacting the dose to move the dose into the needle.

20. The apparatus of claim 1, further comprising a display that provides access to a sample of the dose for assaying the sample of the dose.

21. The apparatus of claim 1, wherein the housing comprises;
a nose;
a terminating member extending outwardly of the nose; and
an engaging member connected to the nose that brings a needle in a coupled relationship with the terminating member.

22. The apparatus of claim 1, wherein at least a portion of the housing comprises a radiation shielding material.

23. The apparatus of claim 1, further comprising a display for observing the dose in the housing without radioactive exposure.

24. The apparatus of claim 23, wherein the dose is viewable through an element that is substantially impervious to radioactive transmission.

25. The apparatus of claim 24, wherein the dose is viewable indirectly through the element.

26. The apparatus of claim 23, wherein the dose is viewable through a light pipe to avoid radioactive exposure.

27. The apparatus of claim 23, wherein the dose is viewable through a prism to avoid radioactive exposure.

28. The apparatus of claim 23, wherein the dose is viewable through a combination of mirrors to avoid radioactive exposure.

29. The apparatus of claim 24, wherein the dose comprises a plurality of component doses, and wherein each component dose of the plurality of component doses is observable at the display.

30. The apparatus of claim 29, wherein each component dose of the plurality of component doses is observable prior to ejection according to the treatment plan.

31. The apparatus of claim 1, further comprising:
a needle grid in the housing; and
an adjustable indicator extending adjustably outwardly from the housing for measuring a distance between the housing and the needle grid and that allows a preselected distance of retraction of the housing to administer the dose at a predetermined location in a tissue.

32. The apparatus of claim 1, wherein the plurality of grooves retrains the dose of radioactive seeds.

33. The apparatus of claim 1, wherein the plurality of grooves are in a parallel relationship with each other and located at a surface of the cylinder, and wherein the cylinder is enclosed in a polycarbonate sleeve to retain the dose of radioactive seeds in the plurality of grooves.

34. The apparatus of claim 24, wherein the element comprises at least one of leaded glass and acrylic.

35. The apparatus of claim 1, wherein all of the plurality of radioactive seeds of the treatment plan are adminstered to a patient in a single medical procedure.

36. The apparatus of claim 1, wherein the housing is loaded with the plurality of radioactive seeds prior to shipment to a physician for administration of the plurality of radioactive seeds to the patient.

37. The apparatus of claim 1, wherein the information comprises spatial information.

38. The apparatus of claim 37, wherein the spatial information comprises rectangular spatial coordinates, three dimensional spatial coordinates, and/or a retraction distance associated with the dose.

39. The apparatus of claim 37, wherein the spatial information comprises rectangular coordinates and retraction distance associated with the dose.

40. An apparatus, comprising:
a housing;
a holder in the housing that contains a dose of radioactive seeds corresponding to a treatment plan; and
wherein the treatment plan comprises a plurality of radioactive seeds;
wherein the housing comprises all of the plurality of radioactive seeds of the treatment plan;
wherein the dose is ejected from the housing;
wherein the housing includes a sterilization passageway that allows sterilant to enter the housing for sterilization of the dose within the housing.

41. The apparatus of claim 40, wherein the sterilant comprises gamma radiation.

42. The apparatus of claim 40, wherein the sterilant comprises at least one of ethylene oxide gas and vaporized hydrogen peroxide.

43. The apparatus of claim 40, wherein the sterilant comprises pressurized steam.

44. A method, comprising the steps of:
arranging within a housing a dose for distribution in tissue in an order corresponding to a treatment plan, wherein the order corresponds to spatial coordinates of the dose that corresponds to the treatment plan;
administering the dose in the tissue from the housing in accordance with the treatment plan; and
indicating on the housing spatial coordinates for the dose according to the treatment plan.

45. The method of claim 44, further comprising the step of generating a treatment plan for distribution of a dose.

46. The method of claim 44, further comprising the step of indicating on the housing an identity of the dose.

47. The method of claim 44, further comprising the steps of indicating on the housing a location of a grid for the administration of a dose.

48. The method of claim 44, further comprising the step of indicating on the housing a retraction distance for the dose.

49. The method of claim 44, further comprising the step of measuring a retraction distance of a dose in accordance with the treatment plan.

50. The method of claim 44, further comprising the step of including within the housing the dose corresponding to the treatment plan for one or more patients.

51. The method of claim 44, further comprising the step of indicating on the housing three-dimensional coordinates of each of a plurality of radioactive seeds of the dose as specified in the treatment plan.

52. The method of claim 44, further providing the step of observing information about the dose at the housing without radioactive exposure.

53. The method of claim 44, further comprising the step of displaying through the housing a sample of the dose for assaying.

54. The method of claim 44, wherein the step of arranging further comprises the steps of:
arranging the dose in grooves on a cylinder in the housing;
selectively aligning the grooves with a channel in a stalk connected to the housing; and
moving at least a portion of the dose through the channel and into a needle aligned with the channel.

55. The method of claim 44, further comprising the step of controlling the housing with either a right hand or a left hand when administering the dose.

56. The method of claim 54, wherein the step of moving further comprises the step of moving the dose into tissue through the needle that is operatively coupled to the housing.

57. A method, comprising the steps of:
arranging a plurality of component doses according to an order of the treatment plan;
observing information about each of the plurality of component doses prior to ejection from the housing; and
loading a plurality of needles with the dose from the housing according to the treatment plan;
wherein the step of loading the plurality of needles with the dose from the housing according to the treatment plan comprises the steps of:
aligning the dose with a gated aperture in the housing;
moving the dose into the housing; and
automatically sealing the gated aperture after the dose is loaded in the housing.

58. The method of claim 57, further comprising the steps of:
engaging a hub of one of the plurality of needles to move the one of the plurality of needles in a coupled relationship with the housing; and
ejecting a portion of the dose into the one of the plurality of needles.

59. The method of claim 58, wherein the step of ejecting further comprises the steps of:
moving a stylus through a gate and through the housing to move the dose into a needle of the plurality of needles; and
automatically sealing the gate upon withdrawal of the stylus.

60. The method of claim 57, wherein the step of loading further comprises the step of loading a dose that is a continuous strand.

61. The method of claim 60, wherein the strand comprises at least one radioactive seed.

62. The method of claim 57, further comprising the step of controlling the housing with either a right hand or a left hand when loading the needle with the dose.

63. An apparatus, comprising:
a housing;
a holder in the housing that receives a dose for a treatment positioned in an order corresponding to a treatment plan;
a display on the housing and associated with the dose;
wherein the dose is ejected from the housing;
wherein the display comprises a first subcomponent display and a second subcomponent display;
wherein the first subcomponent display provides information for the dose according to the treatment plan;
wherein the second subcomponent display allows a user to indirectly view the dose without radioactive exposure.

64. The apparatus of claim 63, wherein the display is a slide button coupled to the housing and slidable between a first position and a second position and wherein in the first position, information about the dose is observable, and wherein in the second position access to the dose is provided to assay the dose.

65. The apparatus of claim 63, wherein the information about the dose comprises spatial information.

66. The apparatus of claim 63, wherein the dose comprises one of a plurality of component doses and the information comprises an identity of one of the plurality of component doses.

67. The apparatus of claim 63, wherein the dose that is observable at the second subcomponent display corresponds to an identity of the dose provided at the first subcomponent display.

68. The apparatus of claim 63, wherein the display has an access for assay of the dose.

69. The apparatus of claim 63, wherein the display comprises an element impervious to radioactive transmission; and
wherein the dose is observable through a slot in the housing.

70. The apparatus of claim 63, wherein the dose associated with the display comprises a portion of a dose next in queue for ejection into a needle.

71. The apparatus of claim 64, wherein the display for access comprises a slide button that is slidably coupled to the housing, and wherein the slide button in a first restrained position provided access to assay the dose and in a second restrained position provides information about the dose.

72. The apparatus of claim 63, wherein the holder comprises:
a cylinder having a channel for containing the dose;
a barrel having a wheel and an end connected to the cylinder; and
wherein the barrel is coupled to the housing in a sliding relationship.

73. The apparatus of claim 72, wherein the barrel contains information about the dose that is observable at the display.

74. The apparatus of claim 73, wherein the information is on a surface of the barrel and accessible at the display by selective rotation of the wheel for observing information about the dose.

75. The apparatus of claim 73, wherein the dose comprises a plurality of component doses, and wherein the information accessible at the display corresponds to a one of the plurality of component doses of the treatment plan.

76. The apparatus of claim 63, further comprises:
the housing having a nose and a body, the nose of the housing extending from the body of the housing;
a terminating member comprising a base operatively connected to the housing and selectively engageable with the holder to selectively position the barrel in alignment with the display for providing access to information associated with the dose; and
a stalk extending away from the base and outwardly of an end of the nose; and
wherein the stalk includes a channel aligned with the holder to receive a dose ejected from the housing.

77. The apparatus of claim 76, further comprising an engaging member connected to the end of the housing for engaging an end of a needle to bring it into coupled relationship with an end of the stalk.

78. The apparatus of claim 77, wherein the engaging member further comprises:
an extendable connecting member; and
an actuator that guides the extendable connecting member to engagement with an end of the needle.

79. The apparatus of claim 78, wherein extension of the extendable member moves the extendable member away from the needle and retraction of the extendable member converges a forked end of the extendable member upon the needle near a hub of the needle and draws the hub of the needle in a coupled relationship with the stalk.

80. The apparatus of claim 72, further comprising:
an end cap connected to an end of the housing, the end cap having an annular shoulder extending inwardly of the end of the housing and relieving in a sliding coupled connection an end of the cylinder and a channel extending longitudinally through the end cap; and
the channel in the end cap axially aligned with the channel in the cylinder and the channel in the stalk defining a pathway for loading the dose in the housing and ejecting the dose from the housing.

81. The apparatus of claim 80, further comprising:
an automatically adjustable indicator extending longitudinally through the housing and having a thread end extending through the end cap and a spring biased extension member extending outwardly of an opposed end thereof and the nose of the housing to measure a retraction measurement associated with the dose.

82. The apparatus of claim 63, wherein the dose contained in the holder is positioned in an order corresponding to spatial coordinates of the dose that corresponds to the treatment plan.

83. The apparatus of claim 63, wherein the dose comprises a plurality of component doses, and wherein each dose of the plurality of component doses comprises a continuous linked strand having at least one radioactive seed and at least one spacer.

84. An apparatus, comprising:
a housing configured to be handheld in either a left or right hand;
a holder in the housing that contains a dose of radioactive seeds corresponding to a treatment plan;
wherein the treatment plan comprises a plurality of radioactive seeds;
wherein the housing comprises all of the plurality of radioactive seeds of the treatment plan;
wherein the ejection of the dose from the housing is effected according to the treatment plan.

85. The apparatus of claim 84, further comprising a guide on a surface of the housing for receiving a hand positioned to control the housing when loading a needle with the dose.

86. The apparatus of claim 85, wherein the guide comprises a pair of tapered portions defining an opposed pair of areas on the surface of the housing for receiving either a left hand or a right hand; and
wherein the apparatus further comprises an actuator on the housing positioned for engagement with either the right hand or the left hand for connecting the needle to the housing.

87. An apparatus, comprising:
means for containing within a housing a plurality of component doses of radioactive seeds corresponding to a treatment plan, wherein the treatment plan comprises a plurality of radioactive seeds, wherein the housing comprises all of the plurality of radioactive seeds of the treatment plan;
means for displaying information for the dose according to the treatment plan and the one of the plurality of component doses prior to ejecting the one of the plurality of doses from the housing; and
means for ejecting one of the plurality of component doses from the housing.

88. The apparatus of claim 87, further comprising means for displaying information associated with the one of the plurality of component doses.

89. The apparatus of claim 87, further comprising means for restraining the plurality of component doses within the housing prior to and after ejecting the one of the plurality of component doses.

90. The apparatus of claim 87, wherein the means for ejecting comprises:
means for aligning the one of the component doses in a pathway extending through the housing; and
means for moving the one of the plurality of component doses through the pathway and out of the housing.

91. The apparatus of claim 90, comprising means for coupling the housing to a needle to receive the one of the plurality of component doses to be ejected from the housing.

92. The apparatus of claim 87, further comprising:
means for configuring the housing to be hand held with either the right hand or the left hand; and
means for controlling the housing with either the right hand or the left hand when connecting the housing to a needle and ejecting the one of the plurality of component doses from the housing.

93. The apparatus of claim 88, wherein the means for displaying information associated with the one of the plurality of component doses comprises:
means for displaying an identity of the one of the plurality of component doses.

94. An apparatus, comprising:
a housing;
a holder in the housing that contains a dose of radioactive seeds and adapted for use in a brachytherapy treatment plan;
wherein the holder comprises a cylinder having a plurality of grooves;
wherein the dose is ejected from the housing;
wherein the housing comprises a sterilization passageway that allows sterilant to enter the housing for sterilization of the dose within the housing.

95. An apparatus, comprising:

a housing;

a cylinder in the housing that contains a dose of radioactive seeds corresponding to a treatment plan, the dose comprising a plurality of component doses including at least one of discrete radioactive seeds and a continuous strand of radioactive seeds;

the cylinder having a grooves in an outer surface thereof receive the dose;

a sleeve surrounding the cylinder, the sleeve restraining the dose in the grooves of the cylinder;

a first gate at a first end of the cylinder and a second gate at a second end of the cylinder opposed from the first end of the cylinder, the first gate and the second gate restraining the dose within the grooves;

a terminating member connected to the first end of the housing, the terminating member having a channel aligned selectively with each groove in the cylinder and adapted to be coupled to at least one needle;

a first display component that provides spatial information for each of the plurality of component doses according to the treatment plan;

a second display component that discloses a one of the component doses next to be ejected from the housing.

96. An apparatus, comprising:

a housing;

a cylinder in the housing that contains a dose of radioactive seeds corresponding to a treatment plan, the dose comprising a plurality of component doses including at least one of discrete radioactive seeds and a continuous strand of radioactive seeds;

the cylinder having grooves in an outer surface thereof that receive the dose;

a sleeve surrounding the cylinder, the sleeve retraining the dose in the grooves of the cylinder;

a first gate at a first end of the cylinder and a second gate a second end of the cylinder opposed from the first end of the cylinder, the first gate and the second gate retraining the dose within the grooves;

a terminating member connected to the first end of the housing, the terminating member having a channel aligned selectively with each groove in the cylinder and adapted to be coupled to at least one needle;

a wheel for rotating the cylinder to effect selective alignment of a selected one of the grooves with the channel in the terminating member;

a barrel connected to the wheel and the cylinder, the barrel having information associated with each of the plurality of component doses;

a first display component that provides information about each of the plurality of component doses;

a second display component that discloses a one of the component doses next to be ejected from the housing; and a lock member coupled to the wheel that secures the cylinder in a secured position for each of the plurality of component doses in association with the first display component and the second display component.

97. A method, comprising the steps of:

arranging in a housing a dose of radioactive seeds according to a treatment plan; and loading a plurality of needles with the dose from the housing according to the treatment plan;

arranging a plurality of component doses according to an order of the treatment plan; and observing information about each of the plurality of component doses prior to ejection from the housing;

engaging a hub of one of the plurality of needles to move the one of the plurality of needles in a coupled relationship with the housing; and moving a stylus through a gate and through the housing to move the dose into a needle of the plurality of needles; and automatically sealing the gate upon withdrawal of the stylus ejecting a portion of the dose into the one of the plurality of needles.

98. A method, comprising the steps of:

moving, according to a treatment plan, a dose of radioactive seeds into a housing via a gated aperture, the dose including radioactive seeds and spacers in continuous strands;

automatically sealing the gated aperture after the dose is loaded in the housing;

assaying the radioactivity of at least one of the radioactive seeds to verify a correct arrangement of the dose in the housing according to the treatment plan; and visually inspecting the dose via a display in the housing to verify a correct arrangement of the dose in the housing according to the treatment plan.

99. The method of claim 57, wherein the step of observing information about each of the plurality of component doses prior to ejection from the housing comprise the step of:

observing an identity of one of the plurality of component doses prior to ejection from the housing.

* * * * *